(12) United States Patent
Dersch et al.

(10) Patent No.: US 9,885,053 B2
(45) Date of Patent: Feb. 6, 2018

(54) METHOD OF MERISTEM EXCISION AND TRANSFORMATION

(71) Applicant: Monsanto Technology LLC, St. Louis, MO (US)

(72) Inventors: Erik Dersch, Fitchburg, WI (US); Richard J. Heinzen, N. Freedom, WI (US); Brian J. Martinell, Mt. Horeb, WI (US); Anatoly Rivlin, Brooklyn, WI (US); Yuechun Wan, Madison, WI (US); Xudong Ye, Chesterfield, MO (US)

(73) Assignee: Monsanto Technology LLC, St. Louis, MO (US)

( * ) Notice: Subject to any disclaimer, the term of this patent is extended or adjusted under 35 U.S.C. 154(b) by 387 days.

(21) Appl. No.: 14/578,112

(22) Filed: Dec. 19, 2014

(65) Prior Publication Data

US 2015/0121574 A1    Apr. 30, 2015

Related U.S. Application Data

(60) Continuation of application No. 13/727,575, filed on Dec. 26, 2012, now Pat. No. 8,937,216, which is a
(Continued)

(51) Int. Cl.
*C12N 15/82* (2006.01)
*A01H 4/00* (2006.01)
(Continued)

(52) U.S. Cl.
CPC ......... *C12N 15/8201* (2013.01); *A01H 4/003* (2013.01); *A01H 4/008* (2013.01);
(Continued)

(58) Field of Classification Search
CPC ............... A01H 4/003; C12N 15/8209; C12N 15/8201; C12N 15/8271; C12N 15/8277;
(Continued)

(56) References Cited

U.S. PATENT DOCUMENTS 1,849,786 A   3/1932  Bloede et al.
2,283,449 A   5/1942  Meneux et al.
(Continued)

FOREIGN PATENT DOCUMENTS

BR   9917361   5/2011
CN   1302900 A   7/2001
(Continued)

OTHER PUBLICATIONS

U.S. Appl. No. 14/642,671, filed Mar. 9, 2015, Calabotta et al.
(Continued)

*Primary Examiner* — Kent L Bell
(74) *Attorney, Agent, or Firm* — Dentons US LLP; David Lanzotti, Esq.

(57) ABSTRACT

The present invention relates to excision of explant material comprising meristematic tissue from cotton seeds. Methods for tissue preparation, storage, transformation, and selection or identification of transformed plants are disclosed, as are transformable meristem tissues and plants produced by such methods, and apparati for tissue preparation.

12 Claims, 8 Drawing Sheets

Related U.S. Application Data continuation of application No. 13/217,228, filed on Aug. 24, 2011, now abandoned, which is a division of application No. 12/045,502, filed on Mar. 10, 2008, now Pat. No. 8,044,260.

(60) Provisional application No. 60/915,066, filed on Apr. 30, 2007, provisional application No. 60/894,096, filed on Mar. 9, 2007.

(51) Int. Cl.
   *C12N 5/04* (2006.01)
   *G01N 33/00* (2006.01)
   *C12N 9/10* (2006.01)

(52) U.S. Cl.
   CPC ............ *C12N 5/04* (2013.01); *C12N 9/1029* (2013.01); *C12N 15/8202* (2013.01); *C12N 15/8205* (2013.01); *C12N 15/8209* (2013.01); *C12N 15/8271* (2013.01); *C12N 15/8274* (2013.01); *C12N 15/8275* (2013.01); *C12N 15/8277* (2013.01); *C12N 15/8281* (2013.01); *G01N 33/0098* (2013.01); *C12Y 203/01081* (2013.01)

(58) Field of Classification Search
   CPC ... C12N 15/8275; C12N 5/04; G01N 33/0098
   USPC ............... 800/278, 293, 294, 314; 536/23.1; 435/430, 430.1
   See application file for complete search history.

(56) References Cited

U.S. PATENT DOCUMENTS

| | | | |
|---|---|---|---|
| 3,104,692 A | 9/1963 | Turner | |
| 3,301,292 A | 1/1967 | O'Connor | |
| 3,667,523 A | 6/1972 | Lynn et al. | |
| 3,744,399 A | 7/1973 | Boneil | |
| 4,066,012 A | 1/1978 | Satake et al. | |
| 4,220,287 A | 9/1980 | Boczewski | |
| 4,245,553 A | 1/1981 | Nakamura | |
| 4,301,183 A | 11/1981 | Giguere | |
| 4,326,358 A | 4/1982 | Lawrence et al. | |
| 4,530,278 A | 7/1985 | Sarig et al. | |
| 4,986,997 A | 1/1991 | Posner et al. | |
| 5,004,863 A | 4/1991 | Umbeck | |
| 5,015,580 A | 5/1991 | Christou et al. | |
| 5,073,675 A | 12/1991 | Jones et al. | |
| 5,164,310 A | 11/1992 | Smith et al. | |
| 5,217,902 A | 6/1993 | Jones et al. | |
| 5,250,313 A | 10/1993 | Giguere | |
| 5,262,316 A | 11/1993 | Engler et al. | |
| 5,286,635 A | 2/1994 | Hanson et al. | |
| 5,368,778 A | 11/1994 | Shimotomai et al. | |
| 5,379,952 A | 1/1995 | Geiger | |
| 5,538,880 A | 7/1996 | Lundquist et al. | |
| 5,550,318 A | 8/1996 | Adams et al. | |
| 5,563,055 A | 10/1996 | Townsend et al. | |
| 5,567,599 A | 10/1996 | Lemieux | |
| 5,591,616 A | 1/1997 | Hiei et al. | |
| 5,678,477 A | 10/1997 | Satake et al. | |
| 5,693,512 A | 12/1997 | Finer et al. | |
| 5,731,179 A | 3/1998 | Komari et al. | |
| 5,767,366 A | 6/1998 | Sathasivan et al. | |
| 5,824,877 A | 10/1998 | Hinchee et al. | |
| 5,846,797 A | 12/1998 | Strickland et al. | |
| 5,914,451 A | 6/1999 | Martinell et al. | |
| 5,952,230 A | 9/1999 | Kim et al. | |
| 5,981,840 A | 11/1999 | Zhao et al. | |
| 6,070,815 A | 6/2000 | Miyatake | |
| 6,140,555 A | 10/2000 | Reichert et al. | |
| 6,153,813 A | 11/2000 | Reichert et al. | |
| 6,265,638 B1 | 7/2001 | Bidney et al. | |
| 6,307,127 B1 | 10/2001 | Jorsboe et al. | |
| 6,384,301 B1 | 5/2002 | Martinell et al. | |
| 6,422,137 B1 | 7/2002 | Nakhei-Nejad | |
| 6,581,535 B2 | 6/2003 | Barry et al. | |
| 6,900,057 B2 | 5/2005 | Burns et al. | |
| 6,936,294 B2 | 8/2005 | Satake et al. | |
| 7,002,058 B2 | 2/2006 | Martinell et al. | |
| 7,057,089 B2 | 6/2006 | Ranch et al. | |
| 7,067,834 B2 | 6/2006 | Horigane et al. | |
| 7,150,993 B2 | 12/2006 | Davis et al. | |
| 7,154,027 B2 | 12/2006 | Demmer et al. | |
| 7,229,034 B2 | 6/2007 | Feazel et al. | |
| 7,279,336 B2 | 10/2007 | Gelvin et al. | |
| 7,288,694 B2 | 10/2007 | Armstrong et al. | |
| 7,345,218 B1 * | 3/2008 | Jiao ........................ | A01H 4/005 800/294 |
| 7,402,734 B2 | 7/2008 | Martinell et al. | |
| 7,560,611 B2 | 7/2009 | Adams et al. | |
| 7,658,033 B2 | 2/2010 | Martinell et al. | |
| 7,694,457 B2 | 4/2010 | Martinell et al. | |
| 7,888,552 B2 | 2/2011 | Ye et al. | |
| 7,935,529 B2 | 5/2011 | Davis et al. | |
| 7,937,890 B2 | 5/2011 | Adams et al. | |
| 8,030,544 B2 | 10/2011 | Martinell et al. | |
| 8,044,260 B2 | 10/2011 | Dersch et al. | |
| 8,323,974 B2 | 12/2012 | Davis et al. | |
| 8,362,317 B2 | 1/2013 | Calabotta et al. | |
| 8,609,934 B2 | 12/2013 | Fillatti et al. | |
| 8,937,216 B2 * | 1/2015 | Dersch ................... | A01H 4/003 800/278 |
| 2002/0120961 A1 | 8/2002 | Ranch et al. | |
| 2002/0184663 A1 | 12/2002 | Sun et al. | |
| 2002/0192040 A1 | 12/2002 | McKinnis | |
| 2003/0018995 A1 | 1/2003 | Dresselhaus et al. | |
| 2003/0074686 A1 | 4/2003 | Heinz et al. | |
| 2004/0034889 A1 | 2/2004 | Khan | |
| 2004/0043117 A1 | 3/2004 | Cope et al. | |
| 2005/0042305 A1 | 2/2005 | Endo et al. | |
| 2005/0044595 A1 | 2/2005 | Arias et al. | |
| 2005/0158699 A1 | 7/2005 | Kadkade et al. | |
| 2006/0005273 A1 | 1/2006 | Rudrabhatla et al. | |
| 2006/0059589 A1 | 3/2006 | Martinell et al. | |
| 2006/0260012 A1 | 11/2006 | Khan | |
| 2007/0039075 A1 | 2/2007 | Tissot et al. | |
| 2011/0271410 A1 | 11/2011 | Adams et al. | |
| 2012/0054918 A1 | 3/2012 | Dersch et al. | |
| 2013/0198899 A1 | 8/2013 | Calabotta et al. | |
| 2015/0007370 A1 | 1/2015 | Adams et al. | |
| 2015/0184170 A1 | 7/2015 | Calabotta et al. | |
| 2017/0238489 A1 | 8/2017 | Adams et al. | |

FOREIGN PATENT DOCUMENTS

| | | |
|---|---|---|
| CN | 1838995 A | 9/2006 |
| EP | 0 298 722 | 1/1989 |
| EP | 0 339 577 | 4/1989 |
| EP | 0 356 987 | 8/1989 |
| EP | 0 380 055 | 8/1990 |
| EP | 0 740 897 B1 | 11/1999 |
| EP | 0 958 863 | 11/1999 |
| EP | 1 142 489 | 10/2001 |
| EP | 1 236 801 | 9/2002 |
| GB | 402848 | 12/1933 |
| GB | 439399 | 12/1935 |
| GB | 657644 | 9/1951 |
| GB | 861711 | 2/1961 |
| GB | 1 459 551 | 12/1976 |
| JP | 59-082063 | 5/1984 |
| JP | 10-276748 | 10/1998 |
| JP | 11-164678 | 6/1999 |
| JP | 2001-17107 | 1/2001 |
| JP | 292717 | 10/2001 |
| JP | 2002-119886 A | 4/2002 |
| JP | 2003339395 | 12/2003 |
| JP | 2004357547 | 12/2004 |
| WO | WO 92/15675 | 9/1992 |
| WO | WO 95/06722 | 9/1995 |
| WO | WO 96/10341 | 4/1996 |
| WO | WO 98/01575 | 1/1998 |
| WO | WO 99/02267 | 1/1999 |

(56) References Cited

FOREIGN PATENT DOCUMENTS

| WO | WO 99/10513 | 3/1999 |
| WO | WO 99/20776 | 4/1999 |
| WO | WO 00/42207 | 7/2000 |
| WO | WO 2000/077230 | 12/2000 |
| WO | WO 01/29241 | 4/2001 |
| WO | WO 02/00010 | 1/2002 |
| WO | WO 02/37987 | 5/2002 |
| WO | WO 02/066599 | 8/2002 |
| WO | WO 03/017752 | 3/2003 |
| WO | WO 03/100381 | 12/2003 |
| WO | WO 2004/000006 | 12/2003 |
| WO | WO 2005/000471 | 1/2005 |
| WO | WO 2005/122750 | 12/2005 |
| WO | WO 2006/026466 | 3/2006 |
| WO | WO 2007/079538 | 7/2007 |
| WO | WO 2007/103769 | 9/2007 |

OTHER PUBLICATIONS

Perry et al., "Rapid isolation of *Arabidopsis thaliana* developing embryos," *BioTechniques* 35:278-282, 2003.
Office Action regarding Brazilian Application No. PI0513090-5, dated Aug. 23, 2016.
Harrell et al., "Automated, in vitro harvest of somatic embryos," *Plant Cell, Tissue and Organ Culture* 39:171-183, 1994.
USPTO: Non-Final Office Action regarding U.S. Appl. No. 14/642,671, dated Oct. 27, 2016.
U.S. Appl. No. 14/314,963, Adams et al.
Abdelnour-Esquivel et al., "Cryopreservation of zygotic embryos of *coffea* spp", *Cryo Letters* 13(5):297-302, 1992.
Aitken-Christie et al., "Automation and Environmental Control in Plant Tissue Culture," *Kluwer Academic Publishers*, Netherlands, 1995.
Aragao et al., "Germ line genetic transformation in cotton (*Gossypium hirsutum* L. by selection of transgenic meristematic cells with a herbicide molecule," *Plant Sci.*, 168(5):1227-1233, 2005.
Baker et al., "High frequency somatic embryogenesis in peanut (*Arachis hypogaea* L.) using mature, dry seed," *Plant Cell Reports* 15:38-42, 1995.
Bechtold et al., "The maternal chromosome set is the target of the T-DNA in the in planta transformation of *Arabidopsis thaliana*," *Genetics*, 155:1875-1887, 2000.
Birch, R. G., "Plant Transformation: Problems and Strategies for Practical Application," *Annu. Rev. Plant Physiol. Plant Mol. Biol.*, 48:297-326, 1997.
Bouchez et al., "A binary vector based on basta resistance for in planta transformation of *Arabidopsis thaliana*," *Comptes Rendus des Seances de L'Academie des Sciences*, Series II: Science de la Vie, 316(1):1188-1193, 1993.
Bretagne-Sagnard et al., "Selection of transgenic flax plants is facilitated by spectinomycin," *Transgenic Res.*, 5: 131-137, 1996.
Broothaerts et al., "Gene transfer to plants by diverse species of bacteria," *Nature*, 433(7026):629-633, 2005.
Buchheim et al., "Maturation of Soybean Somatic Embryos and the Transition of Plantlet Growth," *Plant Physiol.*, 89:768-775, 1989.
Chai et al., "Optimum moisture contents of seeds stored at ambient temperatures," *Seed Science Research* 8, (Supplement 1), 23-28, 1998.
Chandra et al., "Regeneration and genetic transformation of grain legumes: An overview," *Current Science*, 84:(3)381-387, 2003.
Chaudhary et al., "Slow desiccation leads to high-frequency shoot recovery from transformed somatic embryos of cotton (*Gossypium hirsutum* L. cv. Coker 310 FR)," *Plant Cell Rep.*, 21:955-960, 2003.
Chen et al., "A comparison of methods for delivering DNA to wheat: the application of wheat dwarf virus DNA to seeds with exposed apical meristems," *Transgenic Res.*, 1:93-100, 1992.
Chen et al., "Factors influencing agrobacterium-mediated transformation of *monocotyledonous* species," *In Vitro Cell Dev. Biol.*, 40:31-45, 2004.
Chen, Database WPI Week 200432, Oct. 21, 2003.
Chengalrayan et al., "High-frequency conversion of abnormal peanut somatic embryos," *Plant Cell Reports*, 16:783-786, 1997.
Delporte et al., "Plant regeneration through callus initiation from thin mature embryo fragments of wheat," *Plant Cell, Tissue and Organ Culture*, 67:73-80, 2001.
Finer et al., "Transformation of soybean via particle bombardment of embryogenic suspension culture tissue," *In Vitro Cell. Dev. Biol.*, 27:175-182, 1991.
Francois et al., "Different approaches for multi-transgene-stacking in plants," *Plant Sci.*, 163:281-295, 2002.
Grandison et al., "Separation Process in the Food and Biotechnology Industries, Principles and Applications," *Woodhead Publishing Limited*, 266-286, 1995.
Green et al., "Plant regeneration from tissue cultures of maize," *Crop Sci.*, 15:417-421, 1975.
Haris et al, "Transformation of cotton (*Gossypium hirsutum* L.) with insect resistant gene by particle bombardment and agrobacterium," *Pakl. J. of Biological Sci.*, 1(3):170-174, 1998.
Hewezi et al., "Dehydrating immature embryo split apices and rehydrating with agrobacterium tumefaciens: a new method for genetically transforming recalcitrant sunflower," *Plant Mol. Biol. Reporter*, 20:335-345, 2002.
Higley et al., "Effects of non-destructive tissue extraction on the viability of corn, soybean, and bean seeds", *Seed Science and Technology*, 22(2):245-252, 1994.
Hinchee et al., "Production of transgenic soybean plants using agrobacterium-mediated DNA transfer," *Bio/Technology*, 6:915-922, 1988.
Hussain et al., "Sonication assisted agrobacterium mediated transformation (SAAT): an alternative method for cotton transformation," *Pak. J. Bot.*, 39(1):223-230, 2007.
Ibaraki et al., "Automation of somatic embryo production," *Plant Cell, Tissue and Organ Culture*, 65:179-199, 2001.
Johnston et al., "Mass Isolation of Viable Wheat Embryos," *Nature*, 179:160-161, 1957.
Jones et al., "Effective vectors for transformation, expression of heterologous genes, and assaying transposon excision in transgenic plants," *Transgenic Res.*, 1:285-297, 1992.
Kameswara, "Plant genetic resources: Advancing conservation and use through biotechnology," *African J of Biotech*: vol. 3(2); pp. 136-145; Feb. 2004.
Kern, "Comparison between Wheat Embryos Isolated Mechanically and by Floating off from Organic Solvents," *Biologia Plantarum* (*PRAHA*), 17(4):309-313, 1975.
Kingsley, "Introductory Plant Biology," *The McGraw-Hill Companies Inc.*, Eighth Edition, 2000.
Kofer et al., "PEG-mediated plastid transformation in higher plants," *In Vitro Cell Dev. Biol.—Plant*, 34:303-309, 1998.
Krysan, "Ice-Cap. A high-throughput method for capturing plant tissue samples for genotype analysis," *Plant Physiology*, 135:1162-1169, 2004.
Kumar et al., "Stable transformation of the cotton plastid genome and maternal inheritance of transgenes," *Plant Mol. Biol.*, 56:203-216, 2004.
Kumlehn et al., "In vitro development of wheat (*Triticum aestivum* L.) from zygote to plant via ovule culture," *Plant Cell Reports*, 16:663-667, 1997.
Lacorte et al., "Transient expression of GUS and the 2S albumin gene from Brazil nut in peanut (*Arachis hypogaea* L.) seed explants using particle bombardment," *Plant Cell Reports*, 16:619-623, 1997.
Larkin et al., "Transgenic white clover. Studies with the auxin-responsive promoter, GH3, in root gravitropism and lateral root development," *Transgenic Res.*, 5:325-335, 1996.
Laurie et al., "A novel technique for the partial isolation of maize embryo sacs and subsequent regeneration of plants," *In Vitro Cellular and Development Biology—Plant*, 35:320-325, 1999.
Li et al., "Improvement of cotton fiber quality by transforming the acsA and acsB genes into *Gossypium hirsutum* L. by means of vacuum infiltration," *Plant Cell Rep.*, 22:691-697, 2004.

(56) References Cited

OTHER PUBLICATIONS

Lim et al., "Construction of small binary vectors for agrobacterium-mediated transformation in plants," *J. of Plant Biol.*, 42(4):317-320, 1999.
Lim et al., "Expression of the glutathione S-transferase gene (NT107) in transgenic dianthus superbus," *Plant Cell, Tissue and Organ Culture*, 80:277-286, 2005.
Livingstone et al., "Efficient transformation and regeneration of diverse cultivars of peanut (*Arachis hypogaea* L.) by particle bombardment into embryogenic callus produced from mature seeds," *Molecular Breeding*, 5:43-51, 1999.
Lowe et al., "Germline transformation of maize following manipulation of chimeric shoot meristems," *Bio/Technology*, 13:677-682, 1995.
Mahalakshmi et al., "Exogenous DNA Uptake via Cellular Permeabilization and Expression of Foreign Gene in Wheat Zygotic Embryos," *Plant Biotechnology*, 17(3)235-240, 2000.
Malone-Schoneberg et al., "Stable transformation of sunflower using Agrobacterium and split embryonic axis explants," *Plant Science*, 103:199-207, 1994.
Marcus et al., "The Wheat Embryo Cell-Free System," *Methods of Enzymology*, 30:749-754, 1974.
Matthys-Rochon, "In vitro development of maize immature embryos: a tool for embryogenesis analysis," *Journal of Experimental Botany* 49(322):839-845, 1998.
McCabe et al., "Stable transformation of soybean (*Glycine max*) by particle acceleration," *Bio/Technology*, 6:923-926, 1988.
McCabe et al., "Tranformation of elite cotton cultivars via particle bombardment of meristems," *Bio/Technology*, 11:596-598, 1993.
McKersie et al., "Application of artificial seed technology in the production of hybrid alfalfa (*Medicage sativa* L.)," *In Vitro Cell Dev. Biol.*, 25:1183-1188, 1989.
Miki et al., "Procedures for introducing foreign DNA into plants," In: Methods in Plant Molecular Biology and Biotechnology, Glick et al. (Eds.), CRC Press, Inc., Boca Raton, FL, pp. 67-88, 1983.
Moon et al., "Effects of proliferation, maturation, and desiccation methods on conversion of soybean somatic embryos", *In vitro Cellular & Developmental Biology—Plant* 39(6):623-628, 2003.
Nghi et al., "Performance of a plate mill and a modified Engelberg huller for small-scale dry milling and de-germing of maize," *International Journal of Food Science and Technology*, 29:347-353, 1994.
Oreifig et al., "Development of a non-lethal selection system by using the aadA marker gene for efficient recovery of transgenic rice (*Oryza sativa* L.)," *Plant Cell Reports*, 22:490-496, 2004.
Orlikowska et al., "Effect of in vitro storage at 4° C. on survival and proliferation of two apple root stock," *Plant Cell, Tissue and Organ Culture*, 31:1-7, 1992.
Patnaik et al., "Agrobacterium-mediated transformation of mature embryos of triticum aestivum and triticum durum," *Current Sci.*, 91(3):307-317, 2006.
Paz et al., "Improved cotyledonary node method using an alternative explant derived from mature seed for efficient agrobacterium-mediated soybean transformation," *Plant Cell Rep.*, 25:206-213, 2006.
Pollard et al., "Plant and Cell Tissue Culture," *Methods in Molecular Biology*, vol. 6, 1990.
Popelka et al., "Genetic transformation of cowpea (*Vigna unguiculata* L.) and stable transmission of the transgenes to progeny," *Plant Cell Rep.*, 25:304-312, 2006.
Rohini et al., "Transformation of peanut (*Arachis hypogaea* L.): a non-tissue culture based approach for generating transgenic plants," *Plant Sci.*, 150:41-49, 2000.
Sandvang, "Novel streptomycin and spectinomycin resistance gene as a gene cassette within a class 1 integron isolated from *Escherichia coli*," *Antimicrobial Agents and Chemotherapy*, 43(12):3036-3038, 1999.
Sawahel et al., "Stable Genetic Transformation of Mature Wheat Embryos using Silicone Carbide Fibers and DNA Imbibition," *Cellular and Molecular Biology Letters*, 2:421-429, 1997.

Schnall et al., "Culturing peanut (*Arachis hypogaea* L.) zygotic embryos for transformation via microprojectile bombardement," *Plant Cell Reports*, 12:316-319, 1993.
Schnug et al., "Preparation techniques of small sample sizes for sulphur and indirect total glucosinolate analysis in brassica seeds by X-Ray fluorescence spectroscopy," *Fett Sci. Technol.*, 95(9):334-337, 1993.
Schroder et al., "Transformation of brassica napus by using the aadA gene as selectable marker and inheritance studies of the marker genes," *Physiologia Plantarum*, 92:37-46, 1994.
Senaratna et al., "Artificial seeds of alfalfa (*Medicago sativa* L.) induction of desiccation tolerance in somatic embryos," *In Vitro Dev. Biol.*, 26:85-90, 1990.
Senaratna etal., "Dehydration injury in germinating soybean (*Glycine max* L. merr.) seeds," *Plant Physiol.*, 72:620-624, 1983.
Senaratna et al., "Desiccation tolerance of alfalfa (*Medicago sativa* L.) somatic embryos. Influence of abscisic acid, stress pretreatments and drying rates," *Plant Sci.*, 35:253-259, 1989.
Senaratna et al., "Direct DNA uptake during the imbibition of dry cells," *Plant Sci.*, 79:223-228, 1991.
Sheilds et al., "Use of fungicides in plant tissue culture," *Plant Cell Reports*, 3:33-36, 1984.
Simoens et al., "A binary vector for transferring genomic libraries to plants," *Nucleic Acids Research*, 14(20):8073-8090, 1988.
Statement from Dr. William J. Gordon-Kamm, Sep. 13, 2011.
"Study of tissue culture of immature embryos and plant regeneration n maize," *Journal of Sichuan University* (*Natural Science Edition*), 36(6):1125-1126, Abstract, 1999, (English Translation).
Svab et al., "Aminoglycoside-3' -adenyltransferase confers resistance to spectinomycin and streptinomycin in nicotiana tabacum," *Plant Mol. Biol.*, 14:197-205, 1990.
Svab et al., "High-frequency plastid transformation in tobacco by selection for a chimeric aadA gene," *Proc. Natl. Acad. Sci. USA*, 90:913-917, 1993.
Tang et al., "Regeneration of transgenic loblolly pine (*Pine taeda* L.) from zygotic embryos transformed with *Agrobacterium tumefaciens,*" *Planta*, 213:981-989, 2001.
Töpfer et al., Uptake and Transient Expression of Chimeric Genes in Seed-Derived Embryos, *The Plant Cell*, 1:133-139, 1989.
Trick et al., "SAAT: sonication-assisted agrobacterium-mediated transformation," *Transgenic Research*, 6:329-336, 1997.
Vertucci et al., "Theoretical basis of protocols for seed storage," *Plant Physiol.*, 94:1019-1023, 1990.
Von Post et al., "A high-throughput DNA extraction method for barley seed," *Euphytica*, 130:255-260, 2003.
Wang et al., "Maize (*Zea mays*) genetic transformation by co-cultivating germinating seeds with agrobacterium tumefaciens," *Biotechnol. Appl. Biochem*, 46:51-55, 2007.
Wilcox, "Soybeans: Improvement, Production, and Uses," *American Society of Agronomy, Crop Science Society of America, Soil Science Society of America*, 1987.
WPI Week Database No. TW558420, dated Oct. 21, 2003.
Xue et al., "A multi-needle-assisted transformation of soybean cotyledonary node cells," *Biotechnol. Lett.*, 28:1551-1557, 2006.
Zambre et al., "Light strongly promotes gene transfer from agrobacterium tumefaciens to plant cells," *Planta*, 216(4):580-586, 2003.
Notice of Allowance regarding U.S. Appl. No. 10/710,067, dated Jan. 29, 2008.
PCT Search Report for Application No. PCT/US2008/056411 dated Oct. 2, 2008.
Notice of Allowance regarding U.S. Appl. No. 11/054,330, dated Dec. 12, 2008.
Notice of Allowance regarding U.S. Appl. No. 12/047,198, dated Oct. 1, 2009.
Notice of Allowance regarding U.S. Appl. No. 12/047,212, dated Oct. 1, 2009.
Notice of Allowability regarding U.S. Appl. No. 12/047,212, dated Mar. 1, 2010.
Notice of Allowance regarding U.S. Appl. No. 12/192,932, dated Aug. 5, 2010.
Notice of Allowance regarding U.S. Appl. No. 11/613,031, dated Sep. 16, 2010.

(56) References Cited

OTHER PUBLICATIONS

Notice of Opposition regarding European Patent No. 1,635,949, dated Oct. 5, 2011.
Office action dated Mar. 9, 2012, in European Patent Application No. 08731808.5.
Office Action issued in European Application No. 11191760.5 dated Apr. 30, 2014.
English translation of office action issued in Chinese Patent Application No. 200880007599.4 dated Aug. 10, 2011.
U.S. Appl. No. 15/452,519, filed Mar. 7, 2017, Adams et al.
Office Action regarding Brazilian Application No. PI0808716-4, dated Feb. 9, 2017, 12 pages.
Barros et al., "Transformação Genética De *Coffea arabica* Através De Bombardeamento," *Biotecnologia* pp. 150-152, 2000.

* cited by examiner

⊥ Peak to valley distance

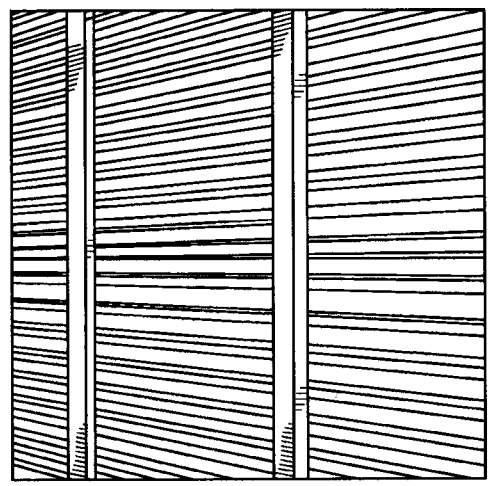
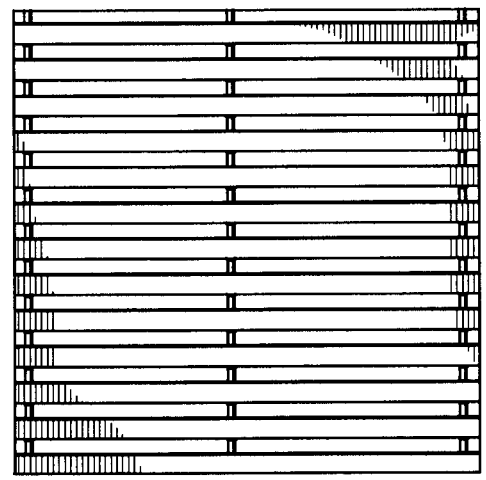
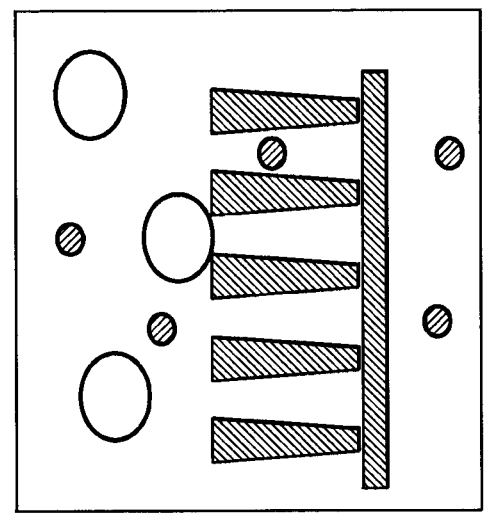
FIG. 3A  V-technology (cross-section)
FIG. 3B  Top view
FIG. 3C  Bottom view

METHOD OF MERISTEM EXCISION AND TRANSFORMATION

This application is a continuation of copending U.S. patent application Ser. No. 13/727,575, filed Dec. 26, 2012, which is a continuation of U.S. patent application Ser. No. 13/217,228, filed Aug. 24, 2011, now abandoned, which is a divisional of U.S. patent application Ser. No. 12/045,502, filed Mar. 10, 2008, now U.S. Pat. No. 8,044,260, issued Oct. 25, 2011, which claims the priority of U.S. Provisional application Ser. Nos. 60/894,096, filed Mar. 9, 2007, and 60/915,066, filed Apr. 30, 2007, each of the entire disclosures of which are herein incorporated by reference.

BACKGROUND OF THE INVENTION

1. Field of the Invention

The invention relates generally to methods for preparing and transforming cotton meristematic plant tissue and subsequent regeneration of transgenic plants.

2. Description of Related Art

Transformed plants may be obtained by delivery of heterologous DNA to meristematic tissue of a plant embryo. The meristematic tissue contains formative plant cells that differentiate to produce multiple plant structures including stem, roots, leaves, germline tissue, and seeds. Plant meristems may be treated, and selected or screened to determine which of those treated meristems have incorporated new genetic information into germline tissue. U.S. Pat. Nos. 6,384,301 and 7,002,058, and U.S. Publication No. 20060059589 describe methods of genetically transforming soybeans (*Glycine max*) using bacterially-mediated gene transfer directly on the meristematic cells of soybean embryos. U.S. Publication 20050005321 describes excision of soybean meristematic tissues from seeds. Isolated cotton meristems and shoot apex tissues have been transformed (e.g. WO9215675; U.S. Pat. No. 5,164,310; McCabe and Martinell, 1993). However, due to the physical and physiological properties of cotton seeds, conditions for excision of meristematic material and transformation to obtain transgenic plants differ from those for soybean.

The current manual process of excision of embryos from imbibed cottonseed is slow and carries an ergonomic burden. In this process, surface sterilized seeds are aseptically handled one at a time with gloved hands. The explant is then carefully excised. In the case of cotton meristems, seeds are carefully oriented in a manner as to eject the embryo with applied force. Even with careful handling of individual seeds, low recovery of usable embryos is common.

Bacterial contamination of embryos after excision is also a significant concern. The increased handling to preserve higher viability and recovery of explants also increases the likelihood of destructive contamination (which will manifest itself in subsequent processing steps). Such contamination can result in significant loss, as a single contaminated explant will contaminate other samples during transformation and tissue culture. This causes loss of yield and/or transformation frequency. Moreover, the manual excision process is extremely labor intensive, time-consuming, and stands as a barrier to a scaling up of the transformation process in which many plants must typically be treated to yield desired results. There thus remains a great need for a process that would increase the availability of transformable cotton embryos without unacceptably increasing total costs and/or timelines of explant preparation for transformation.

SUMMARY OF THE INVENTION

In one aspect, the invention provides a high throughput method for producing transformed cotton tissue comprising: a) mechanically disrupting cotton seeds to obtain a plurality of cotton embryonic meristem explants; and b) contacting the explants with a selected DNA sequence to obtain at least a first explant transformed with the selected DNA. In certain embodiments, the explants are stored at a temperature of between 0-15° C. for between 1 hour and 7 days prior to being contacted with a selected DNA sequence. In other embodiments, the method further comprises the step of regenerating a transgenic cotton plant transformed with the selected DNA from at least the first explant. In certain embodiments, the method does not comprise generating a callus culture from the explant.

In particular embodiments, the transgenic cotton plant arises from transformation of a meristem that results in transformation of germline tissue. In certain embodiments, the resulting plant is non-chimeric. In alternative embodiments, the resulting plant is chimeric.

In certain embodiments, the method further comprises screening the explants prior to contacting the explants with the selected DNA sequence to identify a fraction of explants amenable to transformation with the selected DNA and regeneration of a transgenic plant therefrom. In other embodiments, screening the explants comprises placing mechanically disrupted cotton seeds comprising the explants in an aqueous environment and selecting explants for contacting with the selected DNA based on buoyancy. In yet other embodiments, screening the explants comprises sieving mechanically disrupted cotton seeds to remove the explants from seed coat or cotyledon tissue. Screening the explants may also enrich the fraction of explants amenable to transformation.

In certain embodiments the selected DNA sequence encodes a selectable or screenable marker, or it may code for or otherwise specify an agronomic trait, including environmental adaptability, among other phenotypes. The trait may also specify production of a desired end-product. The method may further comprise selecting or screening for an explant transformed with the selected DNA by contacting the explant with a selective agent, wherein the selectable marker confers tolerance to the selective agent. The method may be defined as comprising regenerating transgenic plant tissue from the explants. The method may further be defined as comprising regenerating chimeric transgenic plant tissue from the explant and selecting or screening for transgenic tissue from the plant tissue. In other embodiments, the method further comprises regenerating a chimeric plant from the explant and selecting or screening for transgenic tissues from the plant. In particular embodiments, the transgenic cotton plant tissue arises from meristem transformation. In certain embodiments, the transgenic cotton plant arises from periclinal transformation.

The method may further relate to selecting or screening for transgenic tissue which comprises contacting the tissue with a selective agent or an agent that yields a screenable phenotype, selected from the group consisting of glufosinate, dicamba, glyphosate, spectinomycin, streptomycin, kanamycin, G418, paromomycin, hygromycin B, imidazolinone, a substrate of GUS, and combinations thereof.

In other embodiments, the method comprises mechanically disrupting cotton seeds by passing the seeds through rollers that crush the seed. In particular embodiments, the rollers comprise secondary grooves. In yet other embodiments, the rollers are comprised of stainless steel.

In particular embodiments, the explants are contacted with a selected DNA sequence, for instance by contacting the explants with a recombinant *Rhizobium* or *Agrobacterium* spp. capable of transforming at least a first cell of the explant with the selected DNA. In particular embodiments the explant is contacted by a recombinant *Agrobacterium* culture grown to an $OD_{660}$ of from about 0.0045 to about 1.4. The pH in which the cotton meristematic tissue is contacted by the *Agrobacterium* cells may, in certain embodiments, be from about 5.0 to about 6.0, up to about 10.0. In some embodiments, the *Rhizobium* or *Agrobacterium* spp. are suspended in the presence of a selective agent active against an untransformed explant prior to contacting the explants with a recombinant *Rhizobium* or *Agrobacterium* spp. In other embodiments, the explants may be contacted with a selected DNA sequence by microprojectile bombardment.

In certain embodiments, following the contacting of explants with a selected DNA sequence, explants are grown in the presence of a selective agent at 35° C., or are grown under lighting conditions that allow for normal plastid development. In other embodiments, explants may be grown in the dark. In particular embodiments, growth at 35° C. is performed for about 1-7 days, such as about 3-5 days; the selective agent is selected from the group consisting of spectinomycin, streptomycin, kanamycin, glyphosate, glufosinate, hygromycin, and dicamba; or the explants are grown under a light intensity of ≥5µ Einsteins, including 5-200 µ Einsteins, 5-130µ Einsteins, or 70-130µ Einsteins with about a 16 hour light/8 dark photoperiod.

In some embodiments, the explants are grown in the presence of a fungicide prior to, during, or subsequent to the contacting of the explants with a selected DNA. In certain embodiments, the explants are grown in the presence of a fungicide and DMSO. In particular embodiments, the explants are grown in the presence of nystatin, thiabendazole, and DMSO. In another aspect, the invention provides an apparatus for high-throughput generation of transformable plant tissue comprising spaced apart rollers comprising secondary grooves for applying a force to cotton seeds passing through the rollers. In certain embodiments, the rollers are spaced from about 2 mm to about 4 mm apart, or about 2.2 mm to about 3.5 mm apart, as measured by peak to valley of opposing rollers. In particular embodiments the rollers are comprised of stainless steel. The apparatus may further comprise a separator for separating cotton meristematic explants from seed coat or cotyledon tissue. In particular embodiment the separator comprises a liquid container for a determining the buoyancy of the transformable plant tissue. The apparatus may further comprise a water and seed containment tray. In particular embodiments, the apparatus may further comprise an automated mechanism for cleaning the apparatus, which controls one or more of the following cleaning steps: (a) applying a sanitizing solution; (b) removing the sanitizing solution; and (c) storing the apparatus under sterile conditions.

BRIEF DESCRIPTION OF THE DRAWINGS

The following drawings are part of the present specification and are included to further demonstrate certain aspects of the present invention. The invention may be better understood by reference to the drawing in combination with the detailed description of specific embodiments presented herein.

(FIG. 1A) seed excision machine, general view; (FIG. 1B) hopper; (FIG. 1C) top view of hopper and rollers; (FIG. 1D) close-up of steel rollers showing "peak to valley" gap distance; (FIG. 1E) side view of rollers.

(FIG. 2A) effect of roller gap size on embryo excision; (FIG. 2B) effect of purification by sieving and floatation on purity of explant fraction; (FIG. 2C) close-up of excised cotton embryo.

FIGS. 3A-3C: Sieve cross-section (V-technology) with (FIG. 3A) side view schematic; (FIG. 3B) top; and (FIG. 3C) bottom views.

DETAILED DESCRIPTION OF THE INVENTION

Figure 1A:
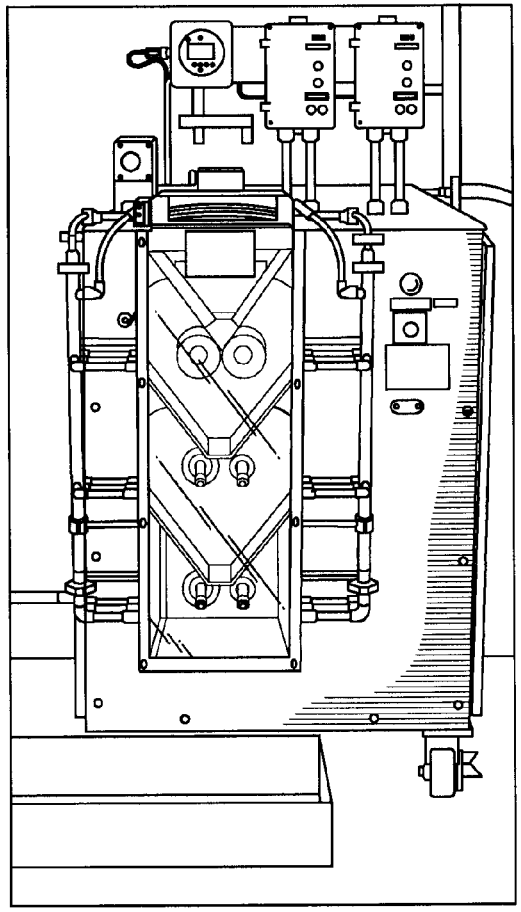
FIGS. 1A-1E: Seed excision machine.
Figure 1B:
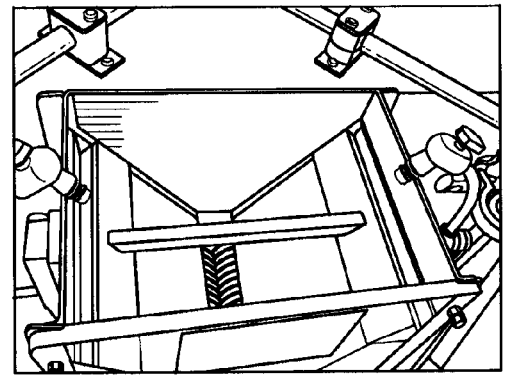
Figure 1C:
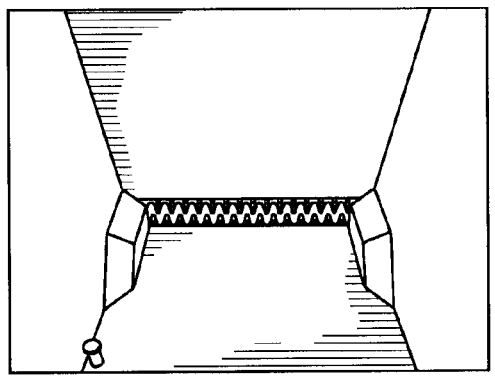
Figure 1D:
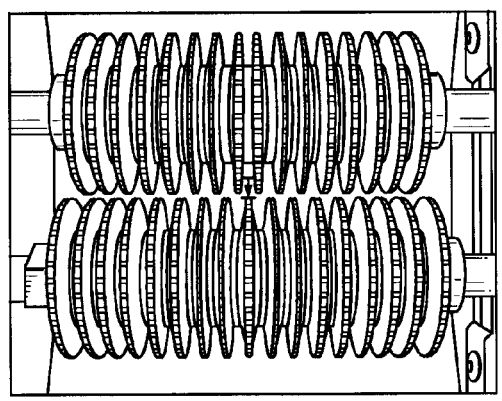
Figure 1E:
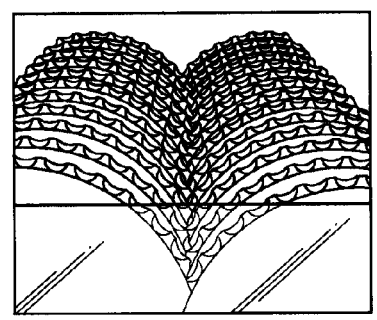

The following is a detailed description of the invention provided to aid those skilled in the art in practicing the present invention. Those of ordinary skill in the art may make modifications and variations in the embodiments described herein without departing from the spirit or scope of the present invention.

The invention provides methods and compositions for preparing, screening, and using cotton explants in automated, high-throughput procedures. These explants may then be transformed by a selected heterologous DNA sequence, and transgenic cotton plants may be regenerated therefrom, without the need for generating a callus cell culture from the transformed explant in order to obtain transgenic progeny plants. The selected heterologous DNA sequence may for instance encode a screenable or selectable marker, and/or comprise a gene of interest specifying a trait exhibited by a cotton plant or cell resulting from the expression of the heterologous nucleic acid. The trait may be agronomically useful, for instance resulting in enhanced yield, pest or pathogen resistance, or environmental adaptability, among other phenotypes. This allows for a fast and efficient mechanized high-throughput process for generating transformed cotton plants. The mechanized process for cotton excision described provides significant monetary, safety and flexibility benefits. Mechanization reduces the estimated man-hours needed to produce 10,000 cotton explants from about 40 to only 2.4 hours, significantly saving labor costs. A lower cost for explants affords greater opportunities for development of improved transformation methods or use of techniques that, while providing benefits such as reduced time to creation of transgenic plants or ability to use elite cultivars for transformation, have to date yield too poor a transformation efficiency to be implemented widely. Such a technique allows larger numbers of transgenes to be tested and higher quality events to be chosen for further analysis, as only a very small number of transformation events are expected to exhibit the most desired expression profiles suitable for commercial development. An improved excision process also allows better timing and scheduling of transformation steps, because of increased flexibility in explant delivery.

The mechanical process described herein can further be easily scaled up to support higher throughput transformation. The potential production rate, assuming 28 hrs of excision per week, is increased from 7,000 explants per person (full time equivalent), by manual excision, to 117,600 per person by the methods described herein. A summary of benefits obtained in specific embodiments of the invention is shown in Tables 14-16. The mechanized processes described herein are also significantly more ergonomically friendly by eliminating repetitive motion typical of the manual excision process. In the case of cotton in which substantial numbers of explants can be required, the benefits are particularly significant.

In order to provide a clear and consistent understanding of the specification and the claims, including the scope given to such terms, the following definitions are provided.

"Embryo" is part of a seed, consisting of precursor tissues (meristematic tissues) for the leaves, stem, and root, as well as one or more cotyledons. Once the embryo begins to grow (germinate), it becomes a seedling plant.

"Meristem" or "meristematic tissue" consists of undifferentiated cells, the meristematic cells, which differentiate to produce multiple plant structures including stem, roots, leaves, germline tissue and seeds. The meristematic cells are the targets for transformation to obtain transgenic plants.

"Explant" is a term used to refer to target material for transformation. Therefore, it is used interchangeably with "meristematic tissue" or "embryo" in the embodiments herein.

"Chimeric plants" are plants that are composed of tissues that are not genetically identical, i.e., the plants will have only a portion or fraction of their tissues transformed, whereas the remainder of the tissues are not genetically transformed.

"Germline transformation" occurs when the gene of interest is transformed into cells that give rise to pollen or ovule thus into seeds.

Seeds from which explants are to be prepared may be harvested from cotton cultivars of interest. Because the methods described do not require embryogenesis or organogenesis, and regeneration of cotton plants, the methods are suited for use with many cultivars, even those known to possess poor embryogenic potential. Thus, in contrast to many prior methods, non agronomically-elite cultivars with good embryogenic potential, such as Coker 312, need not be used to obtain initial $R_0$ transgenic plants. Adjustments may be made to parameters such as imbibition conditions (e.g. temperature and light intensity during seed imbibition), roller gaps and screen sizes to allow for use with cotton seed of various sizes. Seed for excision may be transgenic or non-transgenic. Thus, re-transformation of an already transgenic cotton variety is contemplated.

Prior to imbibition, germination, and/or explant excision, seeds may be subjected to a sterilization step as well as a culling step, to avoid microbial contamination, to remove seeds with a high degree of bacterial or fungal contamination, and also to remove seeds that may for any reason be unlikely to produce viable explant tissue for use with the present invention. Culling may be carried out, for example, based on parameters such as the size, color, or density of the seed or other characteristics, including chemical composition characteristics. Floatation of a seed in an aqueous solution may be utilized to select seed for excision.

Examples of culling methods may include the use of an automatic scale after size sorting or air classification of seed by use of fans and/or a vibratory gravity table to separate seed by weight. Other culling techniques may also be employed including culling by moisture content. A heat treatment may be performed prior to imbibition (e.g. 42-55° C.). Seed priming may be utilized, to control embryonic development prior or after excision. Seeds may also be pre-treated with certain chemical agents, and/or environmental conditions prior to or during imbibition, germination, or excisoin to make the explants more transformable and regenerable after excision.

Imbibition may be done in a clean process, watertight tank (sometimes termed an imbiber), such as a plastic or steel container that can hold seed. A typical capacity would be 1-12.5 kg of dry seed, although other sized containers may be used. Seed imbibition temperature and duration may range, for instance from about 15° C. to about 40° C., such as about 20° C., 23° C., 24° C. or 28° C. Temperature on the lower end of the range may be useful for longer duration imbibition. Duration may range from several hours to 14-48 hours, or several days. In certain embodiments, an imbibition period of about 18 hours may be used.

In specific embodiments, excision is mechanically performed using rollers that crush seeds applied to their faces, which can be counter-rotating, in particular embodiments. The gap between the rollers may be adjusted based on the size of the applied seeds. In certain embodiments where cottonseed is being crushed, the roller gaps may, for instance, be in the range of 2-4.5 mm (as measured peak to valley between the opposing rollers). Roller material may, for instance, be elastomeric or metallic. In certain embodiments, stainless steel rollers have been found to retain beneficial working qualities even following repeated and sustained use. For use with cotton seeds, rollers with secondary grooves have been found to efficiently grip and crush seed with minimal damage to the meristematic explant seed fraction. Excision may also be performed on dry cotton seed. Meristematic tissues obtained therefrom may then be rehydrated and transformed.

Following excision, the invention also provides methods and apparati for screening to separate transformable meristematic explant material from non-transformable damaged explants, cotyledons, seed coats, and other debris. The methods may be performed manually, or may be partially or fully mechanized. In certain embodiments, the screening process is substantially mechanized. For instance, one or more steps of sieving may be performed, using sieves of appropriate size based on size of the seeds being crushed and the explants being isolated. Bulk yield of crushed seed that has passed through the rollers may be put through a series of separation sieves, such that unwanted large and small debris are separated from the desired explant by size exclusion. The sieving screens may be sloped to facilitate movement of plant material. Movement of material along or through the sieves (e.g. embryos and debris) may also be assisted, for instance by water flow including water spray, or by a combination of sieve slope and water spray. Vibration of sieve surfaces may also assist in movement of plant material. Continuous sieving may be performed by using a rotating tumbler made out of an appropriately sized mesh screen. Sieving may be effectively accomplished, for instance with cottonseed material, using U.S. Standard sieves such as: #8 (2.36 mm opening), #10 (2.0 mm opening), #16 (1.18 mm opening), and others as appropriate (e.g. elongated window sieves such as 1/16"×3/4", 1/18"×3/4", 1/19"×1/2", or 1/20"×1/2"). Sieves with other opening sizes may be fabricated as needed, based on the size of material being applied. The length of time for the screening process and the vigor of sieving may also be adjusted to enhance the throughput and/or yield of the process.

The apparatus may further include a seed and water containment system to help maintain sterility as well as a clean in place system, allowing convenient maintenance and cleaning of the machine.

Other screening methods may also be utilized, such as by measuring differential buoyancy in solutions of explant material versus debris. A fraction of material that floats in an aqueous solution has been found to be enriched for intact transformable explants. Combinations of such screening methods may also be used. The fraction of material with transformable explants may comprise both meristematic tissues and other tissues, such as portions of cotyledons. The explant should however contain at least some of the meristematic region such that typically the explant can produce a bud or shoot within 12 weeks of the onset of appropriate growth conditions.

In some embodiments, excised meristematic material may be stored prior to commencement of co-cultivation or other transformation procedure. Parameters that may be varied include temperature, duration, and media used in storage, among others. For instance, explants may be stored submerged in media, for instance INO media or degas sed INO media at 0° C. or greater, e.g. about 4-15° C. Explants may also be stored on filter paper wetted with INO, for instance at 4° C. Media components such as antibiotics, PEG8000, and antioxidants may also be employed. Duration of storage may range, for instance, from one or more hours to overnight, or 1, 2, 3, 4 days or up to 7 days. Storage may serve to adjust the developmental stage of an embryo relative to the time of transformation, as well as to assist in scheduling of excision and transformation procedures, or to allow excised material to recover from mechanical stress of excision. Wet-excised meristematic explants may be dried for storage, followed by rehydration prior to inoculation. Such drying may, for instance, occur prior to or during sieving. Inoculation may be performed, for instance for 10-120 minutes, during which explants are incubated on a shaker with an *Agrobacterium* suspension. The suspension media may be INO, or other media. Following this inoculation step, the suspension is removed and co-culture continues in INO, for example. Anti-apoptotic agents may be used during co-culture, including antipain (1-100 uM); 3-aminobenzamide ((5 uM-4 mM), Ac-DEVD-CHO (0.01-0.1 uM) and Ac-YVAD-CMK (0.01-0.1 uM), or other caspase inhibitor, among others. Plant growth regulators and other agents promoting T-DNA transfer and integration and plant regeneration may also be included to enhance transformation and plant regeneration. Sulfite may also be added to co-culture media, to improve plant tissue health. Antibiotics and antifungal agents, such as streptomycin, spectinomycin, nystatin, and thiabendazole, among others, may be used to supplement the co-culture medium. Co-culture may be carried out in the dark, or under lighting conditions suitable for promoting normal plastid development, such as in a lighted Percival incubator with a 16 hour light/8 hour dark photoperiod under a light intensity of ≥5 µE, such as about 5 µE to about 200 µE. Such lighting conditions may promote gene transfer from *Agrobacterium* (Zambre et al., 2003).

In certain embodiments the excised and screened tissues may be transformed with a heterologous gene of interest. Various methods have been developed for transferring genes into plant tissue including high velocity microprojection, microinjection, electroporation, direct DNA uptake, and bacterially-mediated transformation. Bacteria known to mediate plant cell transformation include a number of species of the Rhizobiaceae, including, but not limited to, *Agrobacterium* spp., *Sinorhizobium* spp., *Mesorhizobium* spp., *Rhizobium* spp., and *Bradyrhizobium* spp. (e.g. Broothaerts et al., 2005; U.S. Patent Application Publication 2007/0271627). Targets for such transformation have often been undifferentiated callus tissues, although differentiated tissue also has been used for transient and stable plant transformation, and may be in this instance.

In designing a vector for the transformation process, one or more genetic components are selected that are introduced into the plant cell or tissue. Genetic components can include any nucleic acid that is introduced into a plant cell or tissue using the method according to the invention. In one embodiment, the genetic components are incorporated into a DNA composition such as a recombinant, double-stranded plasmid or vector molecule comprising at least one or more of following types of genetic components: (a) a promoter that functions in plant cells to cause the production of an RNA sequence, (b) a structural DNA sequence that causes the production of an RNA sequence that encodes a product of agronomic utility, and (c) a 3' non-translated DNA sequence that functions in plant cells to cause the addition of poly-adenylated nucleotides to the 3' end of the RNA sequence.

The vector may contain a number of genetic components to facilitate transformation of the plant cell or tissue and regulate expression of the structural nucleic acid sequence. In one preferred embodiment, the genetic components are oriented so as to express an mRNA that in an optional embodiment can be translated into a protein. The expression of a plant structural coding sequence (a gene, cDNA, synthetic DNA, or other DNA) that exists in double-stranded form involves transcription of messenger RNA (mRNA) from one strand of the DNA by RNA polymerase enzyme and subsequent processing of the mRNA primary transcript inside the nucleus. This processing involves a 3' non-translated region that adds polyadenylated nucleotides to the 3' ends of the mRNA. Means for preparing plasmids or vectors containing the desired genetic components are well known in the art.

Transcription of DNA into mRNA is regulated by a region of DNA usually referred to as the "promoter". The promoter region contains a sequence of bases that signals RNA polymerase to associate with the DNA and to initiate the transcription into mRNA using one of the DNA strands as a template to make a corresponding complementary strand of RNA. A number of promoters that are active in plant cells have been described in the literature. Such promoters would include but are not limited to the nopaline synthase (NOS) and octopine synthase (OCS) promoters that are carried on Ti plasmids of *Agrobacterium tumefaciens*, the caulimovirus promoters such as the cauliflower mosaic virus (CaMV) 19S and 35S promoters and the Figwort mosaic virus (FMV) 35S promoter, and the enhanced CaMV35S promoter (e35S). A variety of other plant gene promoters that are regulated in response to environmental, hormonal, chemical, and/or developmental signals, also can be used for expression of heterologous genes in plant cells, including, for instance, promoters regulated by (1) heat (Callis et al., 1988, (2) light (e.g., pea RbcS-3A promoter, Kuhlemeier et al., (1989); maize RbcS promoter, Schaffner et al., (1991); (3) hormones, such as abscisic acid (Marcotte et al., 1989, (4) wounding (e.g., Wuni, Siebertz et al., 1989); or other signals or chemicals. Tissue specific expression is also known.

As described below, it is preferred that the particular promoter selected should be capable of causing sufficient expression to result in the production of an effective amount of the gene product of interest. Examples describing such promoters include without limitation U.S. Pat. No. 6,437, 217 (maize RS81 promoter), U.S. Pat. No. 5,641,876 (rice actin promoter), U.S. Pat. No. 6,426,446 (maize RS324 promoter), U.S. Pat. No. 6,429,362 (maize PR-1 promoter), U.S. Pat. No. 6,232,526 (maize A3 promoter), U.S. Pat. No. 6,177,611 (constitutive maize promoters), U.S. Pat. Nos. 5,322,938, 5,352,605, 5,359,142 and 5,530,196 (35S promoter), U.S. Pat. No. 6,433,252 (maize L3 oleosin promoter), U.S. Pat. No. 6,429,357 (rice actin 2 promoter as well as a rice actin 2 intron), U.S. Pat. No. 5,837,848 (root specific promoter), U.S. Pat. No. 6,294,714 (light inducible promoters), U.S. Pat. No. 6,140,078 (salt inducible promoters), U.S. Pat. No. 6,252,138 (pathogen inducible promoters), U.S. Pat. No. 6,175,060 (phosphorus deficiency inducible promoters), U.S. Pat. No. 6,635,806 (gamma-coixin promoter), and U.S. patent application Ser. No. 09/757,089 (maize chloroplast aldolase promoter). Additional promoters that may find use are a nopaline synthase (NOS) promoter (Ebert et al., 1987), the octopine synthase (OCS) promoter (which is carried on tumor-inducing plasmids of *Agrobacterium tumefaciens*), the caulimovirus promoters such as the cauliflower mosaic virus (CaMV) 19S promoter (Lawton et al., 1987), the CaMV 35S promoter (Odell et al., 1985), the figwort mosaic virus 35S-promoter (Walker et al., 1987; U.S. Pat. Nos. 6,051,753; 5,378,619), the sucrose synthase promoter (Yang et al., 1990), the R gene complex promoter (Chandler et al., 1989), and the chlorophyll a/b binding protein gene promoter, PClSV (U.S. Pat. No. 5,850,019), and AGRtu.nos (GenBank Accession V00087; Depicker et al, 1982; Bevan et al., 1983) promoters.

Promoter hybrids can also be constructed to enhance transcriptional activity (U.S. Pat. No. 5,106,739), or to combine desired transcriptional activity, inducibility and tissue specificity or developmental specificity. Promoters that function in plants include but are not limited to promoters that are inducible, viral, synthetic, constitutive as described, and temporally regulated, spatially regulated, and spatio-temporally regulated. Other promoters that are tissue-enhanced, tissue-specific, or developmentally regulated are also known in the art and envisioned to have utility in the practice of this invention.

The promoters used in the DNA constructs (i.e. chimeric/ recombinant plant genes) of the present invention may be modified, if desired, to affect their control characteristics. Promoters can be derived by means of ligation with operator regions, random or controlled mutagenesis, etc. Furthermore, the promoters may be altered to contain multiple "enhancer sequences" to assist in elevating gene expression.

The mRNA produced by a DNA construct of the present invention may also contain a 5' non-translated leader sequence. This sequence can be derived from the promoter selected to express the gene and can be specifically modified so as to increase or decrease translation of the mRNA. The 5' non-translated regions can also be obtained from viral RNAs, from suitable eukaryotic genes, or from a synthetic gene sequence. Such "enhancer" sequences may be desirable to increase or alter the translational efficiency of the resultant mRNA. The present invention is not limited to constructs wherein the non-translated region is derived from both the 5' non-translated sequence that accompanies the promoter sequence. Rather, the non-translated leader sequence can be derived from unrelated promoters or genes (see, for example U.S. Pat. No. 5,362,865). Examples of non-translation leader sequences include maize and petunia heat shock protein leaders (U.S. Pat. No. 5,362,865), plant virus coat protein leaders, plant rubisco leaders, GmHsp (U.S. Pat. No. 5,659,122), PhDnaK (U.S. Pat. No. 5,362, 865), AtAnt1, TEV (Carrington and Freed, 1990), and AGRtu.nos (GenBank Accession V00087; Bevan et al., 1983). Other genetic components that serve to enhance expression or affect transcription or translational of a gene are also envisioned as genetic components.

The 3' non-translated region of the chimeric constructs may contain a transcriptional terminator, or an element having equivalent function, and a polyadenylation signal that functions in plants to cause the addition of polyadenylated nucleotides to the 3' end of the RNA. The DNA sequences are referred to herein as transcription-termination regions. The regions are required for efficient polyadenylation of transcribed messenger RNA (mRNA). RNA polymerase transcribes a coding DNA sequence through a site where polyadenylation occurs. Examples of suitable 3' regions are (1) the 3' transcribed, non-translated regions containing the polyadenylation signal of *Agrobacterium* tumor-inducing (Ti) plasmid genes, such as the nopaline synthase (NOS; Fraley et al., 1983) gene, and (2) plant genes such as the soybean storage protein genes and the small subunit of the ribulose-1, 5-bisphosphate carboxylase (ss-RUBISCO) gene. An example of a preferred 3' region is that from the ssRUBISCO E9 gene from pea (European Patent Application 0385 962).

In one embodiment, the vector contains a selectable, screenable, or scoreable marker gene. These genetic components are also referred to herein as functional genetic components, as they produce a product that serves a function in the identification of a transformed plant, or a product of agronomic utility. The DNA that serves as a selection or screening device may function in a regenerable plant tissue to produce a compound that would confer upon the plant tissue resistance to an otherwise toxic compound. A number of screenable or selectable marker genes are known in the art and can be used in the present invention. Genes of interest for use as a selectable, screenable, or scoreable marker would include but are not limited to gus, green fluorescent protein (gfp), luciferase (lux), genes conferring tolerance to antibiotics like kanamycin (Dekeyser et al., 1989) or spectinomycin (e.g. spectinomycin aminoglycoside adenyltransferase (aadA); U.S. Pat. No. 5,217,902), genes that encode enzymes that give tolerance to herbicides like glyphosate (e.g. 5-enolpyruvylshikimate-3-phosphate synthase (EPSPS): Della-Cioppa et al., 1987; U.S. Pat. Nos. 5,627, 061; 5,633,435; 6,040,497; 5,094,945; WO04074443, and WO04009761; glyphosate oxidoreductase (GOX; U.S. Pat. No. 5,463,175); glyphosate decarboxylase (WO05003362 and US Patent Application 20040177399; or glyphosate N-acetyltransferase (GAT): Castle et al., U.S. Patent Publication 20030083480), dalapon (e.g. dehI encoding 2,2-dichloropropionic acid dehalogenase conferring tolerance to 2,2-dichloropropionic acid (Dalapon; WO9927116)), bromoxynil (haloarylnitrilase (Bxn) for conferring tolerance to bromoxynil (WO8704181A1; U.S. Pat. No. 4,810,648; WO8900193A)), sulfonyl herbicides (e.g. acetohydroxyacid synthase or acetolactate synthase conferring tolerance to acetolactate synthase inhibitors such as sulfonylurea, imidazolinone, triazolopyrimidine, pyrimidyloxybenzoates and phthalide; (U.S. Pat. Nos. 6,225,105; 5,767,366; 4,761,373; 5,633,437; 6,613,963; 5,013,659; 5,141,870; 5,378,824; 5,605,011); encoding ALS, GST-II), bialaphos or phosphinothricin or derivatives (e.g. phosphinothricin acetyltransferase (bar) conferring tolerance to phosphinothricin or glufosinate (U.S. Pat. Nos. 5,646,024, 5,561,236, 5,276,268; 5,637,489; 5,273,894; and EP 275,957), atrazine (encoding GST-III), dicamba (dicamba monooxygenase; U.S. Patent Application Publications 20030115626, 20030135879), or sethoxydim (modified acetyl-coenzyme A carboxylase for conferring tolerance to cyclohexanedione (sethoxydim) and aryloxyphenoxypropionate (haloxyfop) (U.S. Pat. No. 6,414,222), among others. Other selection procedures can also be implemented including positive selection mechanisms (e.g. use of the manA gene of *E. coli*, allowing growth in the presence of mannose), and dual selection (e.g. simultaneously using 75-100 ppm spectinomycin and 3-10 ppm glufosinate, or 75 ppm spectinomycin and 0.2-0.25 ppm dicamba) and would still fall within the scope of the present invention. Use of spectinomycin at a concentration of about 25-1000 ppm, such as at about 150 ppm, is also contemplated.

The present invention can be used with any suitable plant transformation plasmid or vector containing a selectable or screenable marker and associated regulatory elements as described, along with one or more nucleic acids expressed in a manner sufficient to confer a particular desirable trait. Examples of suitable structural genes of agronomic interest envisioned by the present invention would include but are not limited to genes for disease, insect, or pest tolerance, herbicide tolerance, genes for quality improvements such as yield, nutritional enhancements, environmental or stress tolerances, or any desirable changes in plant physiology, growth, development, morphology or plant product(s) including starch production (U.S. Pat. Nos. 6,538,181; 6,538,179; 6,538,178; 5,750,876; 6,476,295), modified oils production (U.S. Pat. Nos. 6,444,876; 6,426,447; 6,380,462), high oil production (U.S. Pat. Nos. 6,495,739; 5,608,149; 6,483,008; 6,476,295), modified fatty acid content (U.S. Pat. Nos. 6,828,475; 6,822,141; 6,770,465; 6,706,950; 6,660,849; 6,596,538; 6,589,767; 6,537,750; 6,489,461; 6,459,018), high protein production (U.S. Pat. No. 6,380,466), fruit ripening (U.S. Pat. No. 5,512,466), enhanced animal and human nutrition (U.S. Pat. Nos. 6,723,837; 6,653,530; 6,5412,59; 5,985,605; 6,171,640), biopolymers (U.S. Pat. RE37,543; 6,228,623; 5,958,745 and U.S. Patent Publication No. US20030028917). Also environmental stress resistance (U.S. Pat. No. 6,072,103), pharmaceutical peptides and secretable peptides (U.S. Pat. Nos. 6,812,379; 6,774,283; 6,140,075; 6,080,560), improved processing traits (U.S. Pat. No. 6,476,295), improved digestibility (U.S. Pat. No. 6,531,648) low raffinose (U.S. Pat. No. 6,166,292), industrial enzyme production (U.S. Pat. No. 5,543,576), improved flavor (U.S. Pat. No. 6,011,199), nitrogen fixation (U.S. Pat. No. 5,229,114), hybrid seed production (U.S. Pat. No. 5,689,041), fiber production (U.S. Pat. Nos. 6,576,818; 6,271,443; 5,981,834; 5,869,720) and biofuel production (U.S. Pat. No. 5,998,700). Any of these or other genetic elements, methods, and transgenes may be used with the invention as will be appreciated by those of skill in the art in view of the instant disclosure.

Alternatively, the DNA sequences of interest can affect these phenotypes by encoding a an RNA molecule that causes the targeted inhibition of expression of an endogenous gene via gene silencing technologies such as antisense-, co-suppression-mediated mechanisms, RNAi technologies including miRNA (e.g., U.S. Patent Application Publication 2006/0200878).

Exemplary nucleic acids that may be introduced by the methods encompassed by the present invention include, for example, DNA sequences or genes from another species, or even genes or sequences that originate with or are present in the same species, but are incorporated into recipient cells by genetic engineering methods rather than classical reproduction or breeding techniques. However, the term "exogenous" is also intended to refer to genes that are not normally present in the cell being transformed, or perhaps simply not present in the form, structure, etc., as found in the transforming DNA segment or gene, or genes that are normally present yet that one desires, e.g., to have over-expressed. Thus, the term "exogenous" gene or DNA is intended to refer to any gene or DNA segment that is introduced into a recipient cell, regardless of whether a similar gene may already be present in such a cell. The type of DNA included in the exogenous DNA can include DNA that is already present in the plant cell, DNA from another plant, DNA from a different organism, or a DNA generated externally, such as a DNA sequence containing an antisense message of a gene, or a DNA sequence encoding a synthetic or modified version of a gene.

In one embodiment, transformation of plant tissue is performed by an *Agrobacterium* or other Rhizobia-mediated methods, and the DNA sequences of interest are present on one or more T-DNAs (U.S. Pat. Nos. 6,265,638, 5,731,179; U.S. Patent Application Publications US2005/0183170; 2003110532) or other sequence (e.g., vector backbone) that is transferred into a plant cell. The T-DNAs may be bound by RB and/or LB sequences, and may have one border sequence or two border sequences adjacent. The sequences that may be transferred into a plant cell may be present on one transformation vector in a bacterial strain being utilized for transformation. In another embodiment, the sequences may be present on separate transformation vectors in the bacterial strain. In yet another embodiment, the sequences may be found in separate bacterial cells or strains used together for transformation.

The DNA constructs used for transformation in the methods of present invention generally also contain the plasmid backbone DNA segments that provide replication function and antibiotic selection in bacterial cells, for example, an *Escherichia coli* origin of replication such as ori322, an *Agrobacterium* origin of replication such as oriV or oriRi, and a coding region for a selectable marker such as Spec/Strp that encodes for Tn7 aminoglycoside adenyltransferase (aadA) conferring resistance to spectinomycin or streptomycin, or a gentamicin (Gm, Gent) selectable marker gene. For plant transformation, the host bacterial strain is often *Agrobacterium tumefaciens* ABI, C58, LBA4404, AGLO, AGL1, EHA101, and EHA105 carrying a plasmid having a transfer function for the expression unit. Other strains known to those skilled in the art of plant transformation can function in the present invention.

Bacterially-mediated gene delivery (e.g. *Agrobacterium*-mediated; U.S. Pat. Nos. 5,563,055; 5,591,616; 5,693,512; 5,824,877; 5,981,840) can be made into cells in the living meristem of an embryo excised from a seed (e.g. U.S. Pat. No. 6,384,301). During the co-cultivation step or after, an antifungal and/or antibacterial compound may be utilized. Non-limiting examples of such compounds include Nystatin, PCNB (pentachloronitrobenzene) and thiabendazole, among others. Spectinomycin or streptomycin may also be employed, for instance before, during co-cultivation, or afterwards. In certain embodiments, spectinomycin may be added during co-culture (e.g. 100 or 150 ppm, or up to 300-500 ppm, or up to 1000 ppm), and is optionally not present in the media of later culture steps.

The meristematic region may be cultured in the presence of a selection agent. The selective agent may be "pulsed". That is, the concentration of selective agent being used may be varied at different stages in the pre-culture, co-culture, or subsequent tissue culture process. In certain embodiments, the pulsed selective agent is an aminoglycoside such as spectinomycin. The result of this step is the termination or at least growth retardation of most of the cells into which the foreign genetic construction has not been delivered with the simultaneous formation of shoots, which arise from a single cell or a small cluster of cells including a transformed meristematic cell. Resulting transformed shoots and plants may be chimeric (e.g. periclinal chimeras) or they may be clonally derived. However, once a phenotype-positive plantlet is identified, in certain embodiments the continued use of selective agent(s), also termed "secondary selection," may be avoided. Thus, resulting plants may, in this instance, be chimeric with non-transformed root tissue that grew in the absence of selection, even while the elongated shoot tissue, arising from a meristem contacted with a heterologous nucleic acid, itself may or may not be chimeric. This avoidance of secondary selection may save time, labor, and also may result in significant savings in use of culture media and containers. The meristem can be cultivated in the presence of a selection agent, including, but not limited to auxin-like herbicides such as dicamba, 2,4-D, or MCPA, glufosinate, glyphosate, imidazolinone-class herbicides, acetolactate synthase inhibitors, protoporphyrinogen oxidase inhibitors, and hydroxyphenyl-pyruvate-dioxygenase inhibitors, neomycin, kanamycin, paramomycin, G418, aminoglycosides, spectinomycin, streptomycin, hygromycin B, bleomycin, phleomycin, sulfonamides, streptothricin, chloramphenicol, methotrexate, 2-deoxyglucose, betaine aldehyde, S-aminoethyl L-cysteine, 4-methyltryptophan, D-xylose, D-mannose, benzyladenine-N-3-glucuronidase. Examples of various selectable markers and genes providing resistance against them are disclosed in Miki and McHugh, 2004.

In light of this disclosure, numerous other possible selectable or screenable marker genes, regulatory elements, and other sequences of interest will be apparent to those of skill in the art. Therefore, the foregoing discussion is intended to be exemplary rather than exhaustive.

Use of such selective agents may facilitate the recovery of transformed germline cells in the case of chimeric R0 parent plants, such that fully transformed R1 seed is produced. That is, "chemical pruning," or at least inhibition of growth, of non-transformed tissues of chimeric R0 plants selects for growth and development of transformed tissues that include transformed germline tissues capable of yielding fully transformed plants in a subsequent generation. This can allow for the simplified tissue culture and plant regeneration, for instance by eliminating embryogenesis, making the process much faster, less costly, and applicable to a wider range of cotton genotypes including elite cultivars which are generally difficult to transform, as well as to other plants for which embryogenesis and regeneration procedures are not well developed, if at all. In certain embodiments, germline tissue may be selected for within a chimeric plant or plant part, to yield transformed germline tissue, as noted below.

Alternatively, screenable or scorable markers can be employed to identify transgenic sectors/and or plants. Exemplary markers are known and include β-glucuronidase (GUS) that encodes an enzyme for various chromogenic substrates (Jefferson et al., 1987a; Jefferson et al., 1987b); an R-locus gene, that encodes a product that regulates the production of anthocyanin pigments (red color) in plant tissues (Dellaporta et al., 1988); a β-lactamase gene (Sutcliffe et al., 1978); a gene that encodes an enzyme for that various chromogenic substrates are known (e.g., PADAC, a chromogenic cephalosporin); a luciferase gene (Ow et al., 1986); a xylE gene (Zukowsky et al., 1983) that encodes a catechol dioxygenase that can convert chromogenic catechols; an α-amylase gene (Ikatu et al., 1990); a tyrosinase gene (Katz et al., 1983) that encodes an enzyme capable of oxidizing tyrosine to DOPA and dopaquinone that in turn condenses to melanin; green fluorescent protein (Elliot et al., 1999) and an α-galactosidase.

As is well known in the art, other methods for plant transformation may be utilized, for instance as described by Miki et al., (1993), including use of microprojectile bombardment (e.g. U.S. Pat. No. 5,914,451; McCabe et al., 1991; U.S. Pat. Nos. 5,015,580; 5,550,318; 5,538,880).

A variety of tissue culture media are known that, when supplemented appropriately, support plant tissue growth and development, including formation of mature plants from excised meristems. These tissue culture media can either be purchased as a commercial preparation or custom prepared and modified by those of skill in the art. Examples of such media include, but are not limited to those described by Murashige and Skoog, (1962); Chu et al., (1975); Linsmaier and Skoog, (1965); Uchimiya and Murashige, (1962); Gamborg et al., (1968); Duncan et al., (1985); McCown and Lloyd, (1981); Nitsch and Nitsch (1969); and Schenk and Hildebrandt, (1972), or derivations of these media supplemented accordingly. Those of skill in the art are aware that media and media supplements such as nutrients and growth regulators for use in transformation and regeneration are usually optimized for the particular target crop or variety of interest. Tissue culture media may be supplemented with carbohydrates such as, but not limited to, glucose, sucrose, maltose, mannose, fructose, lactose, galactose, dextrose, or ratios of carbohydrates. Reagents are commercially available and can be purchased from a number of suppliers (see, for example Sigma Chemical Co., St. Louis, Mo.; and PhytoTechnology Laboratories, Shawnee Mission, Kans.). An elevated temperature step (e.g. 1-7 or 3-5 days of culture at 35° C.) may be performed at the beginning of tissue culture, following co-cultivation. Explants may also be grown, for instance during co-culture and selection, under lighting conditions that allow for normal plastid development. Thus, explants may be grown under a light intensity of 5-200μ Einsteins, such as 5-130μ Einsteins, with about a 16 hour light/8 dark photoperiod.

Transgenic plants may be regenerated from a transformed plant cell by methods and compositions disclosed here. When putative transgenic plantlets are identified in culture, they may be transplanted. Growth media following transplantation may include soil, or a soil-less medium in pot or growth plug, such as an OASIS plug, Fertiss™ plug, or Elle-pot. A plant growth regulator, such as Mepiquat pentaborate, may be used to reduce plant size and facilitate handling of large numbers of plants. A transgenic plant formed using *Agrobacterium* transformation methods typically (but not always) contains a single simple recombinant DNA sequence inserted into one chromosome and is referred to as a transgenic event. Such transgenic plants can be referred to as being heterozygous for the inserted exogenous sequence. A transgenic plant homozygous with respect to a transgene can be obtained by sexually mating (selfing) an independent segregant transgenic plant that contains a single exogenous gene sequence to itself, for example an R0 plant, to produce R1 seed. One fourth of the R1 seed produced will be homozygous with respect to the transgene. Germinating R1 seed results in plants that can be tested for zygosity, typically using a SNP assay or a thermal amplification assay that allows for the distinction between heterozygotes and homozygotes (i.e., a zygosity assay).

To confirm the presence of the exogenous DNA or "transgene(s)" in the transgenic plants a variety of assays may be performed. Such assays include, for example, "molecular biological" assays, such as Southern and northern blotting and PCR™; "biochemical" assays, such as detecting the presence of a protein product, e.g., by immunological means (ELISAs and western blots) or by enzymatic function (e.g. GUS assay); pollen histochemistry; plant part assays, such as leaf or root assays; and also, by analyzing the phenotype of the whole regenerated plant.

Once a transgene has been introduced into a plant, that gene can be introduced into any plant sexually compatible with the first plant by crossing, without the need for ever directly transforming the second plant. Therefore, as used herein the term "progeny" denotes the offspring of any generation of a parent plant prepared in accordance with the instant invention, wherein the progeny comprises a selected DNA construct. A "transgenic plant" may thus be of any generation. "Crossing" a plant to provide a plant line having one or more added transgenes or alleles relative to a starting plant line is defined as the techniques that result in a particular sequence being introduced into a plant line by crossing a starting line with a donor plant line that comprises a transgene or allele. To achieve this one could, for example, perform the following steps: (a) plant seeds of the first (starting line) and second (donor plant line that comprises a desired transgene or allele) parent plants; (b) grow the seeds of the first and second parent plants into plants that bear flowers; (c) pollinate a flower from the first parent plant with pollen from the second parent plant; and (d) harvest seeds produced on the parent plant bearing the fertilized flower.

The present invention also provides for parts or the plant produced by the methods of the present invention. Plant parts, without limitation, include fruit, seed, endosperm, ovule, pollen, leaf, stem, and roots. In a preferred embodiment of the present invention, the plant part is a seed.

EXAMPLES

Those of skill in the art will appreciate the many advantages of the methods and compositions provided by the present invention. The following examples are included to demonstrate the preferred embodiments of the invention. It should be appreciated by those of skill in the art that the techniques disclosed in the examples that follow represent techniques discovered by the inventors to function well in the practice of the invention, and thus can be considered to constitute preferred modes for its practice. However, those of skill in the art should, in light of the present disclosure, appreciate that many changes can be made in the specific embodiments that are disclosed and still obtain a like or similar result without departing from the spirit and scope of the invention. All references cited herein are incorporated herein by reference to the extent that they supplement, explain, provide a background for, or teach methodology, techniques, or compositions employed herein.

Example 1

Cotton Seed Sterilization, Hydration, and Excision and Recovery of Meristem Explants A. Cottonseed Sterilization and Hydration Cotton seeds were mechanically processed to excise and isolate their meristematic tissues. In order to obtain transformable meristematic explant material, cotton seeds (e.g. from genotypes STN474 (Stoneville Pedigreed Seed Co., Stoneville, Miss.), Delta Pearl (Delta and Pine Land Co., Scott, Miss.), DP5415, DP393, 00S04 (Delta and Pine Land Co.), SureGrow501 or SureGrow747 (Sure Grow Cotton Seed Company, Maricopa, Ariz.) were processed as follows to separate the embryo, comprising meristematic tissues, from the seed coat and cotyledon(s). Cotton seeds were removed from storage at 4° C. or −20° C. and brought to room temperature. Seeds were weighed out, placed into a sterile imbibition unit, and surface-sterilized in 50% Clorox (sodium hypochlorite) for 5 min. Seeds are then rinsed 3 times with sterile distilled water and were hydrated in a liquid hydration medium (CSM) at 28° C. in the dark for about 18 hrs (range of 14 to 42 hours). Alternatively, the imbibition temperature may be lower, for instance about 23° C. The CSM medium contained 200 mg/L carbenicillin (PhytoTechnology Laboratories, Shawnee Mission, Kans.), 125 mg/L cefotaxime (Midwest Scientific, St. Louis, Mo.), 30 mg/L BRAVO 75 (Carlin, Milwaukee, Wis.) and 30 mg/L Captan 50 (Carlin). Other solutions have also successfully been used to hydrate the cotton seeds, including sterile deionized water or water containing a weak concentration of bleach (typically 50 to 1000 ppm sodium hypochlorite). Following hydration, seeds may be used immediately, or stored at refrigeration temperatures for up to a week prior to further processing.

B. Cottonseed Crushing

A current model of the excision machine is shown in FIG. 1. Surface-sterilized hydrated seeds were loaded un-oriented into the excision machine in batches or continuously through a hopper located at the top of the machine (FIG. 1B, 1C). Mechanical excision of embryos was performed using the excision machine in a dedicated clean suite. The excision machine contains 1 pair of steel rollers for seed crushing. The steel rollers (FIG. 1D, 1E) were modified from those used for soybean meristem excision (e.g. U.S. Application 2005/0005321) by changing material from elastomer to stainless steel, by reducing the number of paired rollers from 3 to 1, and by adding grooves along the roller axis for better cotton seed grabbing and more efficient seed crushing. A comparison of the modified steel rollers with the previously developed elastomer rollers used in soybean embryonic axis excision is presented in Table 1. "Quality explants" is understood to mean explants with viable meristematic tissue (i.e. useful as transformation targets).

TABLE 1

Comparison between modified steel rollers and elastomer roller.

| | Modified steel rollers | Elastomer rollers |
|---|---|---|
| % Yield | 41.6 | 11.5 |
| % Regenerable | 14.3 | 3.5 |
| % Quality explant | 45.8 | 16.6 |
| % GUS positive | 0.5 | 0.2 |
| % with strong near-periclinal gus expression | 0.08 | 0.04 |

Results of tests on machine parameters such as roller gap distance and roller speed are summarized in Tables 2-4. The following exemplary settings were found to work well, among others: roller gap distance of 2.5 mm; right roller rotating clock-wise at setting 40 (arbitrary speed setting number on dial); left roller rotating counter-clockwise at setting 80; water flow rate of 10 L/min.

TABLE 2

Effect of roller gap distance on explant yield.

| Experiment 1 | | | Experiment 2 | | |
|---|---|---|---|---|---|
| Roller gap (mm) | % Yield | % with meristem | Roller gap (mm) | % Yield | % with meristem |
| 2 | 10.4 | 37.1 | 2.2 | 9.5 | 39.1 |
| 2.5 | 12.1 | 48.7 | 2.6 | 11.9 | 52.3 |
| 3 | 11.2 | 32 | 3 | 8.9 | 46 |
| 3.5 | 9.4 | 43.9 | 3.6 | 8.7 | 48.6 |
| | | | 4.1 | 6.6 | 40.6 |

TABLE 3

Effect of roller speed on explant yield.

| Right/left roller speed settings | Recovery of quality explant (%) | % Explant with meristem |
|---|---|---|
| 40/60 | 7 | 27.3 |
| 40/80 | 9.3 | 32.5 |
| 40/100 | 6.3 | 31 |
| 60/80 | 6.2 | 20.3 |
| 60/100 | 9.45 | 31 |
| 80/100 | 7 | 23.2 |

TABLE 4

Effect of water flow rate on explant recovery.

| Water flow rate (L/min) | % Seed crushing | % Recovery | % Recovery of quality explant | % Explant with meristem |
|---|---|---|---|---|
| 5 | 21 | 23.9 | 5.7 | 24 |
| 10 | 24 | 40.8 | 10.4 | 25.4 |
| 15 | 19 | 20.5 | 5.9 | 28.8 |
| 20 | 14 | 18.2 | 4.4 | 24.2 |
| 25 | 14 | 15.0 | 3.5 | 23.1 |

Example 2

Meristematic Explant Separation by Sieving

Figure 2A:
FIGS. 2A-2C: Machine excision and purification of cotton embryos.
Figure 2C:
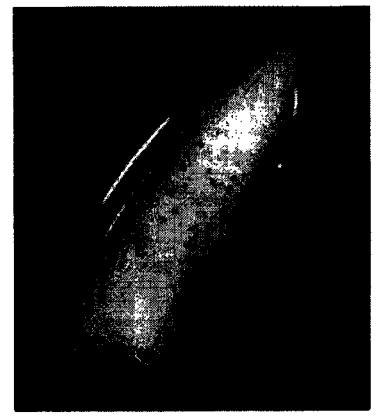
Figure 2B:
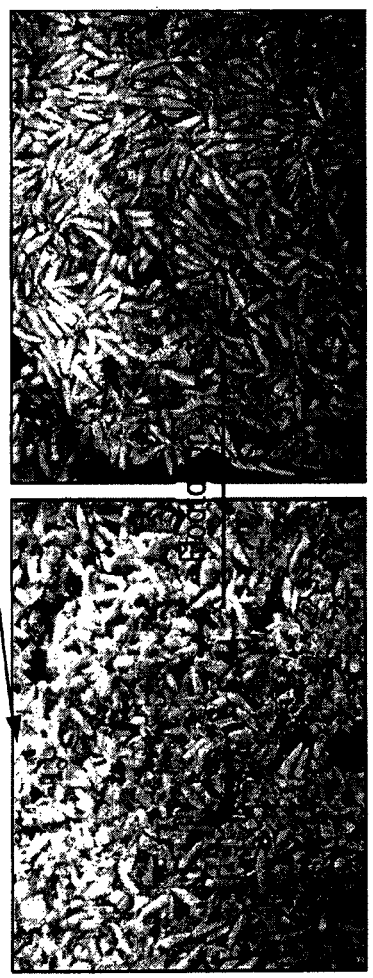

After seed material passed through the roller mechanism, the crushed seed mixture (FIG. 2) was collected by a sieve that allows water to escape but retains crushed seed. The effect of roller spacing on the condition of meristematic tissues from crushed seeds is also shown in FIG. 2. Retained material was then screened to remove debris and enrich for potentially regenerable and transformable explants, comprising meristematic tissues. One method to separate meristematic explants from seed coat and cotyledonary material of the bulk crushed seed was by mechanized or manual sieving, shown in FIG. 2. Various materials were tested in constructing the sieves, including carbon steel screens and stainless steel screens with aluminum, wood, or steel sides. A "V" shaped sieve cross section was found to be easy to manufacture and effective in retaining explants while allowing smaller debris to pass through (FIG. 3). Meristematic explants from crushed seeds could also be efficiently separated by a two-step sieving method, which may be mechanized or manually performed. First, crushed seeds (a mixture of seed coats, cotyledons and embryos) were passed through a #8 screen, which retained large debris (seed coat and cotyledon), while allowing small debris and explants to pass through.

The resulting mixture was then re-sieved using a second stainless steel sieve. Various window sizes, ranging, for instance, from 1/16"×3/8" to 1/24"×1/2" were tested. A window size of 1/18"×3/4" or 1/19"×3/4" gave the best explant purity with minimal additional loss in explant recovery. Thus, sieves with a window size of 1/18"×3/4" or 1/19"×3/4" were chosen for further use in the second sieving step. This parameter may be adjusted based on seed size and expected explant size. The second screen retained explants and some larger debris, but allowed small debris to pass through. Table 5 shows a comparison of resulting material following two sieving steps involving mechanized or hand procedure. In the first instance, an initial manual sieving step was followed by a machine sieving step. In the second instance, both sieving steps were performed by machine. Both hand and machine sieving can separate meristematic explants from other debris. Machine sieving appears to be more efficient than hand sieving in yielding explants useful for transformation.

TABLE 5

Explant recovery using hand and/or machine sieving.

| | $1^{st}$ hand sieving and $2^{nd}$ machine sieving | $1^{st}$ and $2^{nd}$ machine sieving |
|---|---|---|
| Dry seed input (g) | 850 | 300 |
| Crushed mixture output (g) | 96.8 | 34.7 |
| % Yield | 27.8 | 36.2 |
| % Quality explant | 46.4 | 62.1 |

Other parameters that may be varied during the sieving process include the amount of seed (e.g. grams of seed per batch), vigor and length of sieving process (e.g. in minutes), leading to improved purity and yield of transformable material, as measured by the number of "quality explants" per gram of sieved material, or the number of "quality explants" recovered per minute of sieving. "Quality explants" is understood to mean explants with meristems useful as transformation targets. It was observed that the highest process productivity (but not necessarily number of explants) is achieved when a large batch of crushed seed is sieved for a short time. While the absolute number of "quality explants" may be diminished somewhat in this instance, savings of time more than makes up for this. Increased explant purity may also be achieved. This assumes, however, that the amount of available crushed seed is not limiting, due to the relatively small contribution of excision time in the overall length of the process for obtaining transformable cotton explant tissue. Thus, if the amount of seed is limiting, sieving parameters may be adjusted accordingly. Quality explants prepared via the described automated process are ready to be transformed, or may be stored prior to use at refrigeration temperatures, or up to 28° C. prior to use. Storage at these temperatures can maintain quality and transformability for at least 1 week. Refrigeration is preferred for longer storage.

Example 3

Further Enrichment of Recovered Embryonic Explants

The recovered explants from the above example still contained some debris. Explants were further purified by a floatation method. The method was based on the observation that most freshly sieved explants, but not most of the debris, are able to float to the surface of fresh sterile deionized water. This step removed additional debris improving the explant purity (e.g. FIG. 2) and as shown in Tables 6-7. Floatation separation (i.e. with discarding of the sinking fraction) can result in some loss of transformable explants, since both floating and sinking fractions contained transformable explants as judged by subsequent *Agrobacterium*-mediated transient transformation and GUS staining of explant material from each fraction of explants. However, the explant purity of the floating fraction is considerably improved as compared to the material without the floatation step.

TABLE 6

Enrichment of explants by floatation.

| Yield components | 2 step sieving | 2 step sieving + floatation |
|---|---|---|
| % Explant with meristem | 25 | 44 |
| % Damaged explant | 25 | 35 |
| % Debris | 50 | 21 |

TABLE 7

Explant purity enrichment via use of floatation screening step.

| Explant Fraction | % Explants in fraction | Total explants/gram (purity) |
|---|---|---|
| Floating | 57% | 62.7 |
| Sinking | 43% | 14.6 |

Example 4

Further Process Improvements

Figure 4:
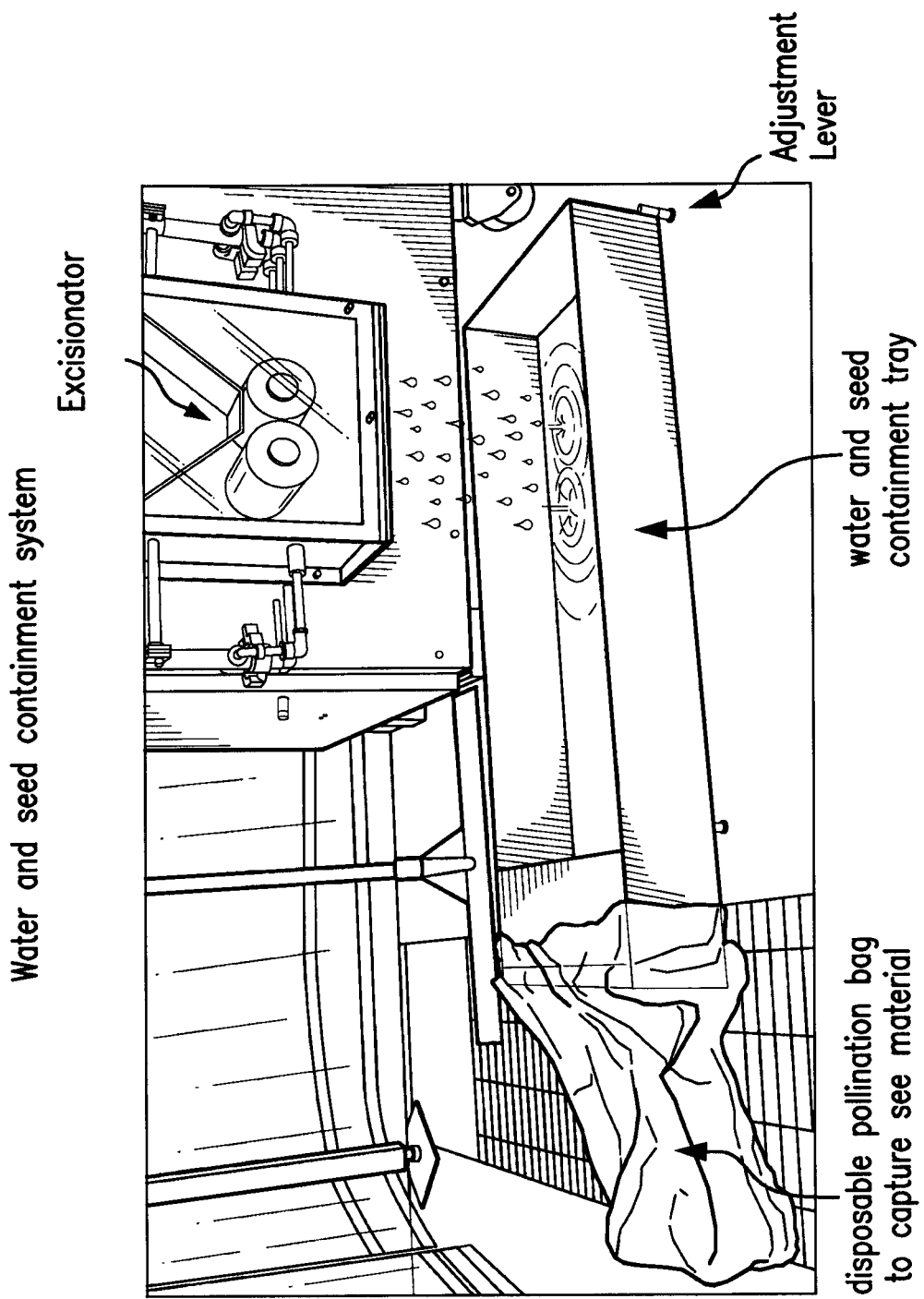
FIG. 4: Excision machine with water and seed containment system.

In order to further improve the efficiency of the process, additional modifications to the "excisionator" are performed. For instance, a water and seed containment tray are added to ensure seed containment (FIG. 4). The tray may, for example, be a rectangular stainless steel tray located under the outlet from the machine, with side walls on three of four sides of the tray. The fourth side contains means for affixing a disposable mesh bag that retains seed and debris while allowing water to escape.

A "clean-in-place" system may also be added to the explant production system, to simplify to simplify cleaning of the equipment, and to reduce the likelihood of workplace accidents and sample contamination. Cleaning procedures involve removal of debris using the flow of sterile water and forceps, if necessary, followed by the pumping of a sanitizing solution (e.g. peracetic acid such as MINNCARE (Minntech, Minneapolis, Minn.)) or gas through the machine for 10 minutes at about 10 L/min. Sanitizing solution is extruded from the machine by application of pressurized sterile air. The cleaned machine is kept, between uses, under positive pressure of sterile air. An automated clean-in-place system has been designed. The mechanism controls the cleaning process in the following manner: first, a sanitizing agent (e.g. 1% MINNCARE or like) is pumped through the equipment for a set period of time (e.g. 10 min or as recommended by the manufacturer of the sanitizing agent). The flow of the agent is then discontinued, and pressurized sterile air is purged through the equipment to remove remaining liquid. Finally, low positive pressure sterile air is applied as a means of sterile storage of the equipment between uses. For the siever, removable parts are autoclaved, while stationary parts may be sprayed with 1% MINNCARE solution or other sterilization solution.

Example 5

Development of a Transformation Method for Cotton Using Excised Embryos

This example describes *Agrobacterium*-mediated transformation of cotton using mechanically excised embryos.

A. Plant Expression Constructs for Transformation:

*Agrobacterium tumefaciens* transformation vectors were constructed using standard molecular biology techniques known to those skilled in the art. The following transformation constructs were used:

(1) pMON96959: which contains the uidA gene under the control of an enhanced CaMV.35Spromoter (U.S. Pat. Nos. 5,322,938; 5,352,605; 5,359,142; and 5,530,1960, a 35S leader sequence, and a 3' non-translated region of the nopaline synthase gene from *Agrobacterium tumefaciens* (Genbank Accession E01312); and the selectable marker Dicamba Mono-Oxygenase (DMO) from *Pseudomonas maltophilia* (U.S. Pat. No. 7,022,896) targeted to chloroplast by a chloroplast transit peptide and the first 24 amino acids of the mature protein from ribulose 1.5-bisphosphate carboxylase small subunit (rbcS) of pea. The DMO gene cassette contains an enhanced promoter for the full length transcript of peanut chlorotic streak virus (PCISV.Flt), a leader sequence from the 5' untranslated region of the Tobacco Etch RNA virus genome (TEV Carrington and Freed, 1990), and a 3' non-translated region of the pea rbcS2 (Coruzzi et al., 1984).

(2) pMON96999: which contains the same uidA cassette as described for pMON96959, but a different selectable marker, an aadA gene (e.g. U.S. Pat. No. 5,217,902) for conferring resistance to spectinomycin. The aadA adenylyltransferase gene product was targeted to the chloroplast by a chloroplast transit peptide of *Arabidopsis* EPSPS (ShkG-CTP2 Klee et al., 1987.), and was under the control of the promoter for *Arabidopsis* elongation factor EF-1alpha (Tsf1; US Patent Application 20050022261) with an FMV-35S enhancer, a Tsf1 leader (exon 1), a Tsf1 intron, and a 3' non-translated region of the pea rbcS2.

(3) pMON102514: which includes DMO and bar genes for use in single or dual selection regimes with dicamba and/or glufosinate. The DMO gene cassette comprises an enhanced promoter for the full length transcript of the peanut chlorotic streak virus (PCLSV.Flt; U.S. Pat. No. 5,850,019), the TEV leader sequence, the 3' untranslated region from the fiber protein E6 gene of sea-island cotton, and *Arabidopsis* chloroplast transit peptide ShkG-CTP2 for targeting DMO to chloroplast. The bar gene cassette contains an enhanced CaMV.35S promoter, a *petunia* Hsp70 leader (U.S. Pat. No. 5,362,865), a bar gene, and an *Agrobacterium* nos terminator.

(4) pMON107303: which contains the uidA gene under the control of an enhanced CaMV.35S promoter, a 35S leader sequence, and a 3' non-translated region of the nopaline synthase gene from *Agrobacterium tumefaciens*; and the bar gene cassette contains the same regulatory elements, but without the chloroplast transit peptide sequence, as those for the aadA cassette in pMON96999.

The examples of transformation constructs described above all contained a single T-DNA for transgene integration into the plant genome. Transformation vectors with 2

T-DNAs have also been used with this invention. An example of such vectors is described below:

(5) pMON107375: carrying 2 T-DNAs, both containing 2 marker genes, in a head-to-tail orientation. The first T-DNA includes an aadA and a uidA cassette. The aadA adenylyl-transferase gene product is targeted to the chloroplast by a chloroplast transit peptide of *Arabidopsis* EPSPS (ShkG-CTP2, Klee et al., 1987.), and the gene is under the control of the promoter for *Arabidopsis* elongation factor EF-1alpha (Tsf1; US Patent Application 2005/0022261) with an FMV-35S enhancer, a Tsf1 leader (exon 1), a Tsf1 intron, and a 3' non-translated region of the pea rbcS2. The uidA gene is under the control of an enhanced CaMV.35S promoter, and a 3' non-translated region of the nopaline synthase gene from *Agrobacterium tumefaciens*. The second T-DNA, consists of a DMO and a bar expression cassette. The DMO gene cassette comprises an enhanced promoter for the full length transcript of the peanut chlorotic streak virus (PCLSV.Flt, U.S. Pat. No. 5,850,019), the TEV leader sequence, the 3' untranslated region from the fiber protein E6 gene of sea-island cotton, and an *Arabidopsis* chloroplast transit peptide ShkG-CTP2 for targeting DMO to chloroplast. The DMO gene was codon optimized for enhanced dicot expression. The bar gene cassette contains an enhanced CaMV.35S promoter, a *petunia* Hsp70 leader (U.S. Pat. No. 5,362,865), a bar gene, and an *Agrobacterium* nos terminator. pMON107353 (oriV), which is similar to pMON107375 (oriRi) except for the origin of replication was also used extensively in the studies described here.

The use of this construct and derived events of interest demonstrate utility of chemical pruning using glufosinate as a means of identifying transgenic plants, and/or positively transformed sectors in chimeric plants, and chemically eliminating negative sectors.

B. Preparation of *Agrobacterium* Cells:

*Agrobacterium* strain C58 containing a binary vector with one or two plant expression cassettes as described above was inoculated, from a glycerol stock, into a liquid LB medium (10 g/L sodium chloride, 5 g/L yeast extract, 10 g/L bacto-tryptone) containing 75 mg/mL spectinomycin and 50 mg/mL kanamycin. The liquid culture was allowed to grow at 28° C. at 200 rpm on a rotary shaker overnight. After the optical density ($OD_{660}$) of the overnight culture reached the target range of 0.4-1.2, the bacterial culture was centrifuged at 3500 rpm for approximately 20-25 min to pellet the cells.

Following removal of the supernatant, the pellet was re-suspended in 10 mL of an inoculation medium (INO, Table 8), and further diluted and adjusted to about 0.28-0.32 at $OD_{660}$. A series of transient GUS expression studies showed that an inoculum $OD_{660}$ of 0.6-0.8 yielded a comparatively higher proportion of meristematic transformation and transgene expression.

TABLE 8

Composition of inoculation medium (INO).

| Ingredient | Amount/L |
|---|---|
| Magnesium sulfate (Fisher M63) | 0.1 g |
| Ammonium sulfate (Fisher A702) | 53.6 mg |
| Sodium phosphate monohydrate (Fisher S369-500) | 60 mg |
| Calcium chloride (Sigma C-3881) | 60 mg |
| Boric acid (Fisher A73-3) | 0.3 mg |
| Manganese sulfate (Sigma I-2550) | 1 mg |
| Zinc sulfate heptahydrate (Sigma Z-1001) | 0.2 mg |
| Potassium iodide (Sigma P-8166) | 0.075 mg |
| Sodium Molybdate dihydrate (Sigma S-6646) | 0.025 mg |
| Cupric sulfate (Fisher C493-500) | 2.5 µg |

TABLE 8-continued

Composition of inoculation medium (INO).

| Ingredient | Amount/L |
|---|---|
| Cobalt chloride hexahydrate (Sigma C-2911) | 2.5 µg |
| Sequestrene (Ciba 964603) | 2.8 mg |
| Potassium nitrate (Sigma P-8291) | 1 g |
| Glucose (Phytotech G386) | 30 g |
| MES (Sigma M8250) | 3.9 g |
| Bring volume to 1 L with de-ionized distilled water | |
| pH with KOH to | 5.4 |
| Autoclave | |
| Add sterile vitamin stock containing the following | |
| Myo-inositol (Sigma I-3011) | 10 mg |
| Nicotinic acid (Sigma N-0765) | 0.1 mg |
| Pyridoxine HCl (Sigma P-8666) | 0.1 mg |
| Thiamine HCl (Sigma T-3902) | 1 mg |

The pH of the *Agrobacterium* preparation medium (growth, resuspension and co-culture media) was found to affect transformation efficiency of excised cotton meristems. A pH of about 5.3 gave the highest subsequent proportion of "high quality" stable transformation events, although media with other pH between 5.0 and 10.0 may be used. "High quality" events refer to transgenic events which contain either a large area of stable GUS expression for instance in one leaf including midvein or stable GUS expression in all or multiple leaves as shown by histochemical GUS assay. Such expression patterns have shown to be more likely correlated with transformation of the L1, L2, or L3 cell layer of meristematic tissue (e.g periclinal transformation), which may result in germline transformation, or suggest single-cell origin of the shoots.

Figure 8:
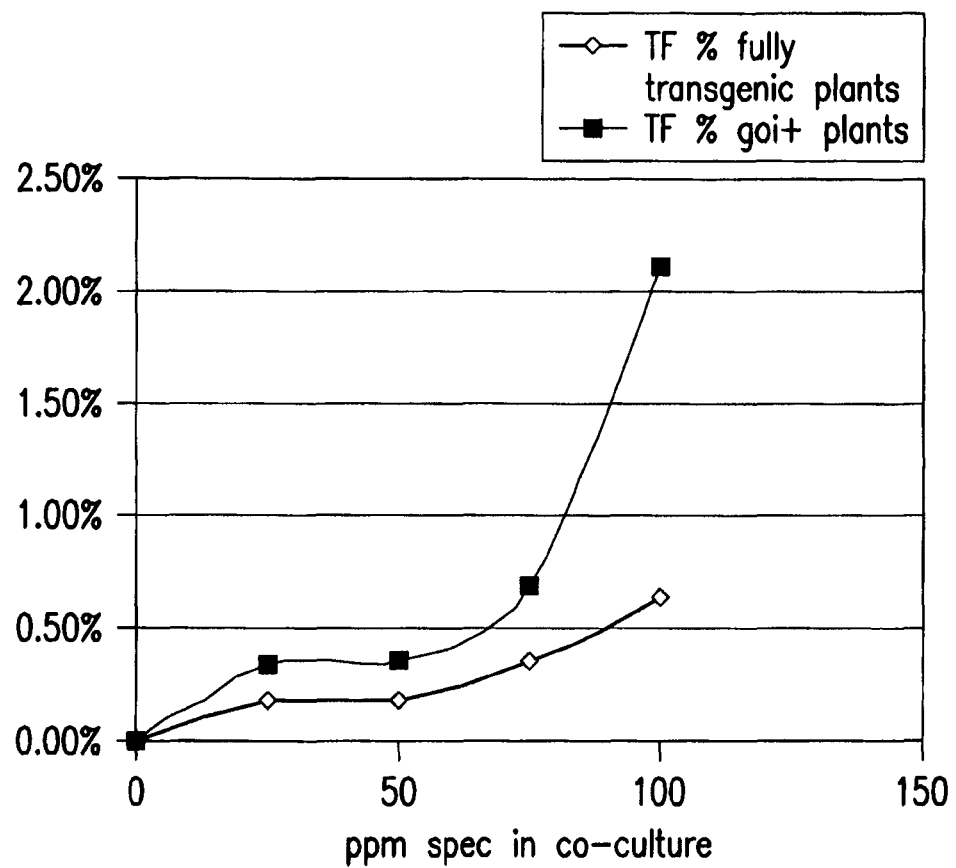
FIG. 8: Increase in transformation frequency (TF) % seen from adding increasing concentrations of spectinomycin to co-culture media.

C. Wounding, Inoculation, and Co-Cultivation of Explants:

Explants from Examples 1 or 2 were rinsed in sterile water. About 1-60 g, e.g. 30 g, of explants was placed into the top part (upside down) of a Plantcon™ container (MP Biomedicals, Solon, Ohio) followed by addition of approximately 50 mL of the prepared *Agrobacterium* suspension, enough to cover the explants. After the Plantcon™ was closed, it was inserted into an appropriately sized holder, which was placed into a sonicator (e.g. L&R Ultrasonics QS140; L&R Manufacturing Co., Kearny, N.J.; or a Honda W113 sonicator, Honda, Denshi Japan). The sonicator was filled with about 2 L of 0.1% Triton® (e.g. Sigma 526-36-23; Sigma Chemical Co, St. Louis, Mo.). After up to 5 min of sonication, the Plantcon™ was placed securely on a shaker at 65-70 rpm or higher for 10 min for incubation. After inoculation, the *Agrobacterium* inoculum was removed from the Plantcon™. About 2 g of the inoculated explant tissue was transferred to a fresh Plantcon™ containing sterile filter paper and 5 mL of INO, and the explants were spread on the medium surface to avoid clustering. The INO medium may also be supplemented with plant growth regulators such as gibberellins (GA3), auxins (e.g. NAA, IBA, IAA, 2,4-D, dicamba, etc), cytokinins (e.g. BAP, thidiazuron, dikegulac, kinetin, etc.), and/or antifungal or antibacterial agents like Nystatin, or thiabendazole (TBZ). The Plantcon™ containing inoculated explants was placed into a Percival incubator for co-cultivation at approximately 22-28° C. and a 16 hour light photoperiod (light intensity ≥5 µE, e.g. between about 5 µE and 200 µE) for 2-5 days. In certain studies, spectinomycin (50-100 ppm) was included in the co-cultivation medium. As shown in FIG. 8, this led to enhanced TF.

D. Selection and Identification of Transgenic Events by Use of Spectinomycin or other Selective Agent in Tissue Culture Medium:

This example describes selection with the antibiotic spectinomycin. However, analogous methods may be performed by using other selection agents such as kanamycin, streptomycin, G418, paromomycin, glufosinate, glyphosate, hygromycin B, imidazolinone, and dicamba, or a combination of any of these or similar selection agents. A screenable marker, such as GUS, CrtB, or a yeast ATP dependent phosphofructokinase (ATP PFK) may also be employed.

Following co-cultivation, explants were removed and implanted into or layered on the surface of a semi-solid WPM medium (Table 9) in Plantcon™ containers supplemented with 200 mg/L cefotaxime, 200 mg/L carbenicillin and 25-200 mg/L spectinomycin with or without plant growth regulators (such as BAP, thidiazuron, GA3 or dikegulac) as needed to stimulate multiple shoot formation. Typically ~25 explants were placed into each container. The results show that surface-plating of explants was at least as effective as implantation (Table 10). Plating of the inoculated explants onto the surface of a liquid WPM medium (Table 9, but without the gelling agent AGARGEL) was also tested to improve efficiency and to reduce ergonomic burden of explant implantation into the medium. Surface plating of explants on liquid culture substrates (filter paper, polyester felt and other fabrics, and other permeable and semi permeable membranes has also been successfully tested. The explants were allowed to grow on the selection medium at 28° C. (daily and seasonal variations 22-33° C.) with a photoperiod of typically 16 hrs light, although 24 hour light is also effective in producing transgenic cotton plants, and light intensity of 5-200 µEinsteins, typically 70-130, for about 4-8 weeks. An initial temperature of 35° C. for the first 3-5 days during selection was also tested, before the explants were moved to 28° C. The culture period at 35° C. was found to be beneficial (e.g. see Example 9).

Regenerating explants with green healthy shoot growth (e.g. FIG. 5) were subsequently transferred into fresh selection medium for continued growth (second selection step). In contrast, explants lacking a gene conferring resistance to spectinomycin yielded bleached shoots or primordia when grown with spectinomycin, which could easily be identified. After 1-4 weeks, plantlets with green healthy looking shoots were transferred and implanted into Cotton Rooting Medium (CRM) (Table 11) for rooting. The rooting medium may comprise spectinomycin or streptomycin, or selection may be discontinued during the rooting step. Rooted plants were then taken to a greenhouse for continued growth and for further analysis.

From *Agrobacterium* infection following explant excision and enrichment, the explants went through the selection process. Selected transgenic events then grew into a mature plant. Transgenic R1 seed can be harvested by about 24 weeks following initiation of a transformation experiment (e.g. *Agrobacterium* co-cultivation), representing significant savings of time and labor as compared to a typical cotton plant transformation and regeneration strategy that employs embryogenesis. Table 12 is illustrative of selection agents and effective rates tested.

TABLE 9

Composition of modified WPM supplemented with antibiotics.

| Ingredient | Amount/L or final concentration |
|---|---|
| LM WPM with vitamins (Phytotech L449) | 2.41 g |
| Dextrose (Fisher D16-3) | 20 g |
| Calcium gluconate (Sigma G-4625) | 1.29 g |
| Clearys 3336 WP (Carlin 10-032) | 0.03 g |
| AGARGEL (Sigma A-3301) | 4 g |
| Fill water to | 1 L |
| pH | 5.6 |
| Autoclave | |
| Carbenicillin (Phytotech C346) (40 mg/mL) | 200 ppm |
| Cefotaxime (Midwest NDC0039-0019-10) (50 mg/mL) | 200 ppm |
| Spectinomycin (50 mg/mL) | 150 ppm |

TABLE 10

Comparison of explant implantation and surface-plating.

| | Implantation | Surface-plating |
|---|---|---|
| Total # explant | 2942 | 2530 |
| % Regenerable | 25.8 | 35.3 |
| % Phenotype positive | 3.0 | 4.7 |
| % Regenerable with GUS | 0.5 | 1.2 |
| % Phenotype positive with GUS | 4.6 | 8.4 |
| % Regenerable with strong near-periclinal gus expression | 0.1 | 0.1 |
| % Phenotype positive with strong near-periclinal gus expression | 1.2 | 0.8 |

Phenotype-positive: demonstrating visible phenotype indicative of resistance to the selective agent used (e.g. green healthy looking properly formed growth on spectinomycin selection as distinct from bleached malformed and necrotic non-transgenic phenotype-negative tissue);
Near periclinal transformation: a large area of 50% or more of cut edge) of stable GUS expression in one leaf including mid-vein, or stable GUS expression in multiple leaves as assayed by histochemical staining for GUS.

TABLE 11

Composition of CRM.

| Ingredient | Amount/L or final concentration |
|---|---|
| MS basal salts (Phytotech M524) | 2.15 g |
| Myo-inositol (Sigma I-3011) | 0.1 g |
| Dextrose (Fisher D16-3) | 30 g |
| SBRM vitamin stock: | 2 mL |
| Glycine (Sigma G-6143): | 1 g/L |
| Nicotinic acid (Sigma N-0765): | 0.25 g/L |
| Pyridoxine HCl (Sigma P-8666): | 0.25 g/L |
| Thiamine HCl (Sigma T-3902): | 0.5 g/L |
| Cysteine (10 mg/mL) | 10 mL |
| Bring volume with deionized distilled $H_2O$ | |
| pH with KOH | 5.8 |
| Bacto agar (BD 214030) | 8 g |
| Autoclave | |
| IAA (Sigma I-2886) (0.02 mg/mL) | 0.1 ppm |
| Timentin (Duchefa T0190) (100 mg/mL) | 100 ppmL |
| Cefotaxime (Midwest NDC0039-0019-10) (50 mg/mL) | 200 ppm |

TABLE 12

Selection agents and their effective rates.

| Selection agent | Tested range (ppm) | Stably transformed plants produced at concentrations (ppm) |
|---|---|---|
| dicamba | 0-10 | 0.3 |
| glufosinate | 0-25 | 0, 4, 5, 7, 10, 13, 25 |
| glufosinate + dicamba | 0-7/0-0.3 | 4/0.2, 4/0.25 |

TABLE 12-continued

Selection agents and their effective rates.

| Selection agent | Tested range (ppm) | Stably transformed plants produced at concentrations (ppm) |
|---|---|---|
| spectinomycin | 0-1000 | 50, 75, 100, 150+ |
| paromomycin | 0-400 | 200, 300 |

Figure 5:
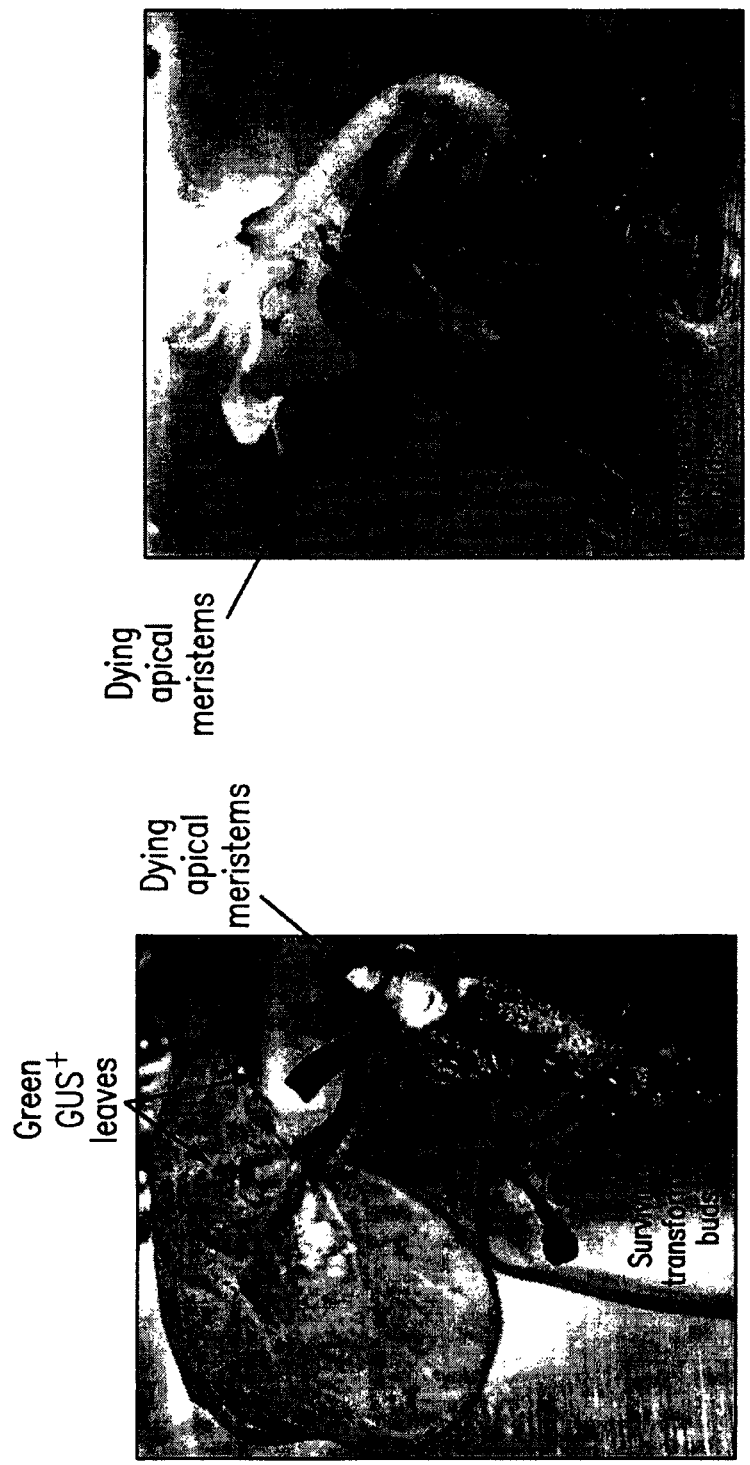
FIGS. 5A-5B: Spectinomycin as a selection agent and visual marker for early identification of transformation. Two views of chimeric transformed cotton tissue (FIG. 5A and FIG. 5B). Non-transformed tissues appear bleached and often malformed under spectinomycin selection, whereas transformed tissues are green and developing properly. Surviving transformed buds are also shown.

Spectinomycin served as a useful visual marker for early identification of transformation. Non-transformed tissues usually appeared bleached and often malformed under spectinomycin selection, whereas transformed tissues were green and properly developing (FIG. 5). The transformed nature of the green tissue was confirmed by GUS expression after about 4-8 weeks on selection media. Therefore, using spectinomycin as a selection agent foregoes the labor intensive and time consuming GUS assays often used in meristem transformation systems and provides the advantage of significantly reducing the labor involved in producing transgenic plants.

E. Selection and Identification of Transgenic Events by Use of Chemical Pruning, or Herbicidal Spray:

Chemical pruning by herbicide spraying, i.e., killing of non-transformed tissue, was also tested on plants that were transformed with transgenes for dicamba and glufosinate tolerance. Plants were placed in a special spray chamber, and hand sprayed with commercial formulations of herbicides such as LIBERTY at 100-3000 ppm, and CLARITY at 100-3000 ppm. Plants were sprayed to run-off, allowed to dry for about 2 hours and then moved back to greenhouse. Non-transgenic tissues were usually killed or their growth was suppressed by the spray, whereas transgene-expressing tissues continued to grow, allowing easy identification of transgenic tissues. CLARITY and LIBERTY sprays often resulted in development of side branches, which became the main growth, leading to R1 seed comprising a transgene.

Similarly, herbicidal sprays have been used to select transgenic plants in the absence of a selection agent, or after an inefficient tissue culture selection. Regenerated events of unknown transgenic status following inoculation with a plasmid containing a herbicide tolerance gene were sprayed with an optimized dose of selective agent (e.g. 1000 ppm glufosinate to obtain resistance phenotype F. Selection and Identification of Transgenic Events by Use of an Analytical Assay:

Plants transformed with a plasmid that contained a visual marker gene such as uidA can be identified by histochemical assays of leaves, pollen, or other tissues, as described in WO9215675; U.S. Pat. No. 5,164,310; McCabe and Martinell, 1993. Real-time PCR may also be utilized.

Example 6

Characterization of Transgenic Events Obtained from Mechanically Excised Cotton Explants This section described the characterization of transgenic events. Event # GH_A24519 is used as an example. Seed (from cotton cv. STN474) were surface sterilized, rinsed, and imbibed in CSM medium for about 16 hours at 28° C. Imbibing seeds were then machine excised using steel rollers set at a 2 to 3 mm gap spacing (measured peak to valley of the opposing rollers, determined to be appropriate for this lot of STN474 seed) and screened by a two step sieving process (manual sieving with a #10 screen followed by automated sieving, and prepared and inoculated with Agrobacterium containing pMON96959, for instance as described in Examples 1-5. Following co-culture, the explants were implanted into WPM solid media supplemented with 100 mg/L cefotaxime and 0.3 mg/L Dicamba at 25 embryos per Plantcon™. Explants were allowed to grow on this selective media for about a month at 28° C. with a 16 hour light photoperiod. GUS assays were performed one month later and several promising plants including GH_A24159 were transferred onto CRM for root development. GUS assays to test for transformation were performed again 3 weeks later, and all sampled leaves showed high level of GUS expression. A cross-section GUS histochemical assay showed GUS expression in vascular tissues of petiole. The first flower from the $R_0$ plant also showed GUS expression in the pollen, petal, sepal and anthers.

Figure 6:
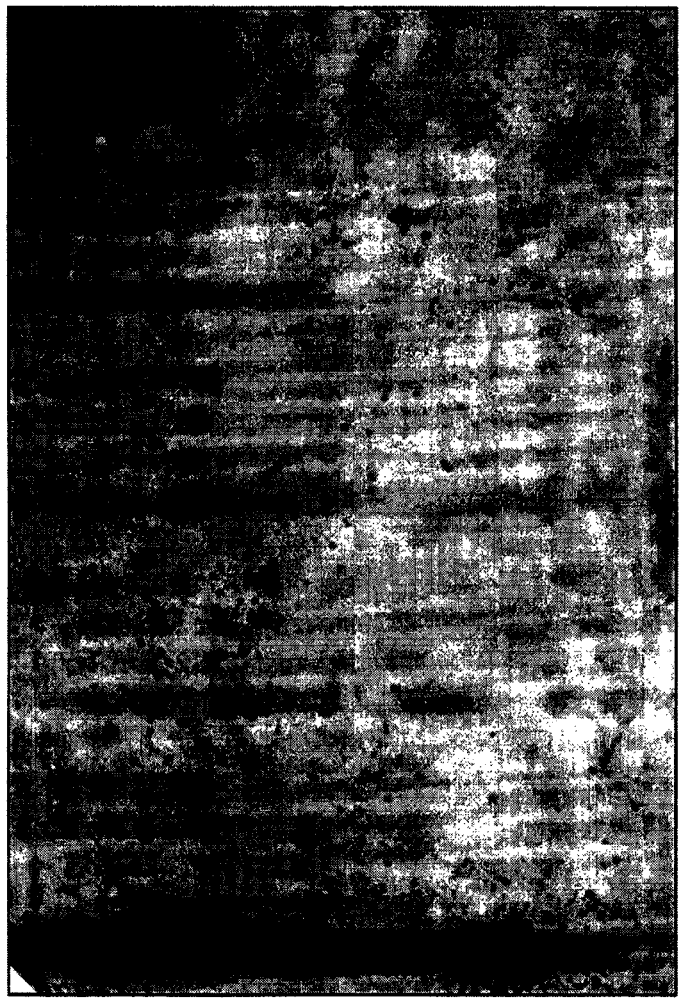
FIG. 6: Southern blot hybridization results confirming transformation, and identification of transgenic machine excised cotton tissue.
Figure 7:
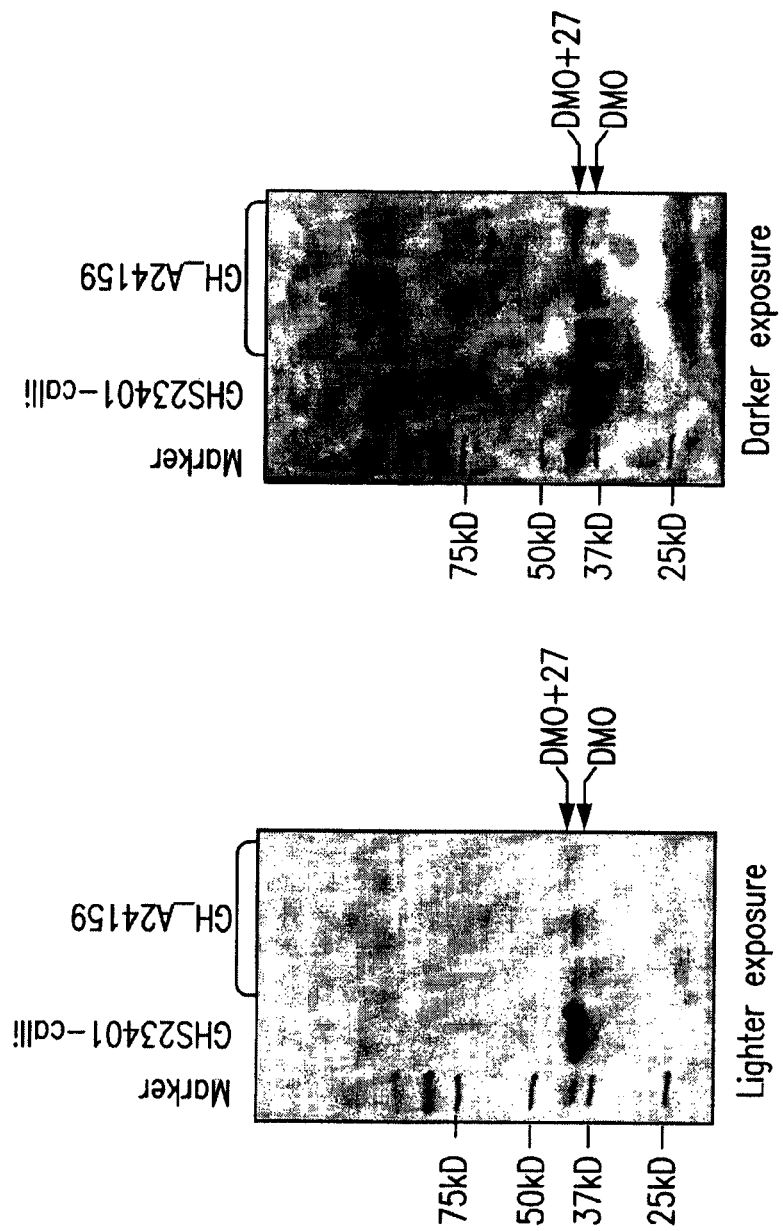
FIG. 7: Western blot, two exposures, demonstrating expression of DMO transgene in cotton tissue derived from machine excised explant.

Molecular analyses were also performed to confirm transformation. PCR results from leaf samples showed the presence of the DMO sequence. Southern blot hybridization analysis of the $R_0$ plant confirmed the presence of at least 2 copies of the DMO transgene in sampled leaves (e.g. lanes 2-4 of FIG. 6). Western analysis further demonstrated DMO protein expression (FIG. 7). Cuttings of the $R_0$ plant were shown to be resistant to 200 ppm CLARITY spray. To speed up R1 analysis, 16-day old immature embryos from the first flower were excised and studied. Eight stained for GUS activity, with six demonstrating GUS expression in all tissues suggesting a 3:1 Mendelian segregation. The remaining flowers were allowed to mature normally to recover R1 seed. Out of 15 R1 seedling plants, 9 were GUS positive. Application of dicamba (200 ppm CLARITY or 3000 ppm CLARITY) further confirmed that GUS+ phenotype and dicamba tolerance was co-segregating in R1 seedlings of GH_A24519.

Mechanized cottonseed embryonic axis excision with modified steel rollers combined with mechanized recovery of explants from crushed seed, and effective selection of transformed material, including "chemical pruning" following Agrobacterium-mediated transformation of wounded explants, has thus allowed the production of transgenic cotton plants within a short period of time, 3 months, with transgenic R1 seed available by 24 weeks after transformation. The time required to obtain transgenic plants and progeny is significantly less than the time required to produce transgenic cotton plants via embryogenesis, resulting plants are fertile, and plants may be obtained in numerous target cotton germplasms of interest, even in lines with poor embryogenic potential. These methods provide the advantage of enhancing process efficiency and robustness, while reducing cost and ergonomic burden.

Example 7

Efficiency of Hand vs Mechanized Excision

The manual process of embryonic axis excision from seed is slow, labor intensive and carries significant ergonomic burden. Use of machine excision in combination with mechanized sieving not only overcomes the above-mentioned problem, but also is up-scalable to increase throughput. Tables 13 and Table 14 show comparisons of hand vs. progressively improved methods of mechanized excision/sieving in excision throughput, and productivity. Productivity for hand excision is based on the assumption of 7 hrs/day, 4 days/week of uninterrupted excision whereas productivity for machine excision is based on the assumption of 1 run (45-75 minutes)/day, 4 days/week. Table 15 shows that mechanized excision/sieving can produce 4000-5000 quality explants i.e., explants with visible meristem, per hour, about a 20-fold improvement over manual excision and provides the advantage of higher throughput and lower ergonomic burden.

TABLE 13

Comparison of excision throughput.

| Excision Method | # Explants produced/man-hour |
|---|---|
| Hand excision | 250 |
| Elastomer rollers & hand sieving | 1400 |
| Steel rollers & hand sieving | 4200 |
| Steel rollers & machine sieving | 4200 |

TABLE 14

Comparison of man-hours needed to produced 10,000 explants/week.

| Excision Method | Man-hours/week |
|---|---|
| Hand excision | 40 |
| Elastomer rollers & hand sieving | 7 |
| Steel rollers & hand sieving | 2.4 |
| Steel rollers & machine sieving | 2.4 |

TABLE 15

Comparison of productivity.

| | Hand excision | Machine excision |
|---|---|---|
| g seed needed to produce 1000 quality explants | 300 | 333 |
| % recovery of quality explants | 32 | 30 |
| Time needed to produce 1000 quality explants | 4 hrs | 14 min |
| Productivity: quality explants/hour | 250 | 4200 |

Example 8

Effect on Transformation of Explant Storage

Storage of machine excised cotton explants was also explored. The ability to store transformation-ready explants would allow more flexibility to schedule and conduct transformation experiments. Following excision, cotton explants may be stored prior to continuing, for instance, with the transformation process. In one experiment, explants were stored overnight at 4° C. after excision, before inoculation with *Agrobacterium*. Explants were found to remain transformation competent after following this storage regimen. Table 16 summarizes the results from another experiment. After explants were recovered for instance as described in Examples 1 and 2 above, they were placed in a sterile Plantcon™ (e.g. ICN Biomedical Cat.#26-720-02) or on filter paper wetted with INO media and placed in a sterile 150 mm Petri dish in a 4° C. cooler in the dark for designated storage time of 0 vs 7 days. The explants were brought to room temperature before inoculation. % Regenerable represents the percentage of total number of explants that were able to grow into a plantlet. % Regenerable with positive GUS refers the number of explant with positive GUS divided by the total number of regenerable explants×100. % Regenerable strong near-periclinal gus expression hits is the number of strong near-periclinal gus expression divided by the total number of regenerable explants×100.

Overall, the results (Table 16) show that storage of explants at 4° C. for 3 days prior to inoculation improved percent recovery of regenerable explants and therefore is a simple and effective method to manage transformation workflow. Even though cold storage seemed to reduce the percentage of GUS expressing plantlets relatively to the number of regenerable explants, those that remained growing were more likely to have stable GUS expression. Consequently, the labor involved in producing transformation events was reduced as well.

TABLE 16

Effect of explant storage on transformation.

| | Days in storage at 4° C. | |
|---|---|---|
| Parameters | 0 | 7 |
| % Regenerable explants | 40.07 | 32.45 |
| % Regenerable with positive GUS | 6.95 | 9.09 |
| % Regenerable with strong near-periclinal gus expression | 2.67 | 2.27 |

Example 9

Effect of Manipulating further Parameters during Imbibition, Co-culture, Selection, and Growth Steps By manipulating one or more of the following parameters such reducing imbibition temperature from 28° C. to 24° C. or 15° C., initial selection of explants at 35° C. for 3 days after co-culture, co-culture under lighting conditions that allow for normal plastid development (e.g. an intensity of ≥5 μE, for instance about 5 μE to about 130-200 μE, under a 16 hour light/8 hour dark photoperiod), use of higher spectinomycin concentration during inoculation/co-culture or selection, use of spectinomycin in co-culture medium, and selecting plants by spraying later (e.g. "chemical pruning" during rooting or later growth), it was possible to increase % germline positive events per explant by 2 to 10 fold. Use of spectinomycin in pre-culture media may also prove beneficial in raising TF (%) or in improving event quality.

In further studies, seed imbibition, and explant excision was performed as noted above (e.g. Example 5) or as in U.S. Patent Publication 20050005321. For inoculation and co-culture, an *Agrobacterium* ABI strain (C58 derivative) harboring a binary vector which carries 1 or 2 T-DNAs and comprising an aadA selectable marker gene and a uidA screenable marker was used. Explants were bulk-sonicated, or sonicated in individual PLANTCON containers. Shoot induction and selection was performed by surface-plating explants on semi-solid selection medium (Table 9) for about 4 weeks. Further shoot induction and rooting was performed by growing explants with green shoots in Oasis® plugs (Smithers-Oasis USA; Kent, Ohio) for shoot elongation and root induction from original radicals in simple liquid medium without selection containing 0.5 g/L WPM salts with vitamins ((Phytotech L449) and 0.25 mg/L IBA for about 2-3 weeks in greenhouse. Results are shown in Table 17. An initial culture temperature of 35° C. was found to be beneficial for production of GUS positive cotton shoots.

TABLE 17

Results from experiments comparing two inoculation/co-culture methods, and two different culture regimes.

| Exp-Trt | Inoc/co-cult. method[1] | Culture temperature | # explants w/ meristem | # GUS+ shoots (total # shoots assayed) | % explants producing GUS+ shoots |
|---|---|---|---|---|---|
| 1021-1 | A | 35° C., 3 d to 28° C. | 127 | 6 (7) | 4.7 |
| 1021-2 | B | 28° C. | 183 | 0 (2) | 0 |
| 1021-3 | B | 35° C., 3 d to 28° C. | 141 | 0 (2) | 0 |
| 1021-4 | A | 28° C. | 324 | 2 (2) | 0.6 |
| 1021-5 | A | 35° C., 3 d to 28° C. | 225 | 7 (9) | 3.1 |
| 1023-1 | A | 35° C., 3 d to 28° C. | 81 | 5 (7) | 6.2 |
| 1023-2 | B | 28° C. | 95 | 0 (0) | 0 |
| 1023-3 | B | 35° C., 3 d to 28° C. | 81 | 11 (13) | 13.6 |
| 1023-4 | A | 28° C. | 101 | 0 (0) | 0 |
| 1023-5 | A | 35° C., 3 d to 28° C. | 88 | 1 (3) | 1.1 |

[1]Method A: All the explants in each treatment were placed in one PLANTCON and *Agrobacterium* inoculum was added to cover the explants. The explants in the inoculum were sonicated (bulk sonication) for 2 min followed by 10 min on shaker (80 rpm). Then the inoculum was removed and the explants were distributed to PLANTCON each containing one piece of filter paper and 5 ml of inoculation medium.
Method B: Explants were distributed to the cover part of each PLANTCON (approximately 100 explants per PLANTCON). Five ml of *Agrobacterium* inoculum was added. The explants were then sonicated for 20 sec, and immediately were transferred along with the inoculum to the bottom part of the PLANTCON, which holds one piece of filter paper.

Example 10

Re-transformation of Roundup Ready™ Cotton Germplasm

Utilizing methods described in this patent, elite transgenic Round-Up Ready™ germplasm may be further transformed utilizing a 2 T-DNA vector (or alternatively two 1 T-DNA vectors) encoding the aadA gene for Spectinomycin selection and employing a new gene (often referred as "the gene of interest;" "GOI") on the second T-DNA to allow segregation away from the aadA as described above. The following cotton method and dataset is useful in describing this "re-transformation".

Cotton RRFlex® seed variety (07W610F) and germplasm control non-transgenic variety (00S04) were compared. Seed was imbibed for ~18 hrs in 24° C., machine excised and machine-sieved (in two steps) following by floatation enrichment of explants. Explants were inoculated with *Agrobacterium* suspension in INO at OD 0.3, sonicated for 2 min, and incubated for 10 min. *Agrobacterium* suspension was then removed and explants distributed into co-culture containers at approximately 2 g per container. Explants were laid onto filter papers wetted with 5 ml of co-culture media (INO with additions of 50 ppm Nystatin, 10 ppm TBZ (thiabendazole), and 100 ppm Spectinomycin) and co-cultured in a lighted Percival incubator at approximately 23 to 25° C. (16 hrs light/8 hrs dark, light intensity ≥5 µE, such as 5 µE to 200 µE) for 3 days. Explants were then transferred onto the selection medium (Table 9), incubated for 3 days in 35° C. in a light room (16 hrs light/8 hrs dark), and then moved to a 28° C. light room (16 hrs light/8 hrs dark). Phenotype positive green plantlets were harvested 6 weeks after inoculation, placed in OASIS plugs wetted with 0.5 g/L WPM salts and moved to green house conditions. Once plants acclimatized and started to grow they were assayed for CP4, GUS, and vascular GUS expression (a predictor of germline transformation). Retransformed transgenic plants were expected to be CP4+ GUS+, while transformed control plants were expected to be CP4– GUS+. An analysis of the yield of transformed plants is listed in Table 18 below. The procedure described can thus be used to re-transform transgenic cotton plants with an efficiency similar to transformation of a conventional non-transgenic cotton variety.

TABLE 18

Transformation frequency observed from re-transformation of transgenic cotton germplasm.

| Cotton Germplasm tested | quality explants inoculated | Spectinomycin phenotype positive (green) plantlets | % green Plantlets | Number of plants sampled for GUS | Plants expressing GUS in all leaves, (germline) | % TF, germline expressing GUS |
|---|---|---|---|---|---|---|
| 00S04 | 928 | 18 | 1.90% | 11 | 2 | 0.22% |
| 07W610F | 3665 | 87 | 2.40% | 64 | 9 | 0.25% |

\* \* \*

All of the compositions and methods disclosed and claimed herein can be made and executed without undue experimentation in light of the present disclosure. While the compositions and methods of this invention have been described in terms of the foregoing illustrative embodiments, it will be apparent to those of skill in the art that variations, changes, modifications, and alterations may be applied to the composition, methods, and in the steps or in the sequence of steps of the methods described herein, without departing from the true concept, spirit, and scope of the invention. More specifically, it will be apparent that certain agents that are both chemically and physiologically related may be substituted for the agents described herein while the same or similar results would be achieved. All such similar substitutes and modifications apparent to those skilled in the art are deemed to be within the spirit, scope, and concept of the invention as defined by the appended claims.

REFERENCES

The following references, to the extent that they provide exemplary procedural or other details supplementary to those set forth herein, are specifically incorporated herein by reference.

U.S. Pat. Nos. 4,761,373; 4,810,648; 5,013,659; 5,015,580; 5,094,945; 5,106,739; 5,141,870; 5,164,310; 5,217,902; 5,229,114; 5,273,894; 5,276,268; 5,322,938; 5,352,605; 5,359,142; 5,362,865; 5,378,619; 5,378,824; 5,463,175; 5,512,466; 5,530,196; 5,538,880; 5,543,576; 5,550,318; 5,561,236; 5,563,055; 5,591,616; 5,605,011; 5,608,149; 5,627,061; 5,633,435; 5,633,437; 5,637,489; 5,641,876; 5,646,024; 5,659,122; 5,689,041; 5,693,512; 5,731,179; 5,750,876; 5,767,366; 5,824,877; 5,837,848; 5,850,019; 5,869,720; 5,914,451; 5,958,745; 5,981,834; 5,981,840; 5,985,605; 5,998,700; 6,011,199; 6,040,497; 6,051,753; 6,072,103; 6,080,560; 6,140,075; 6,140,078; 6,166,292; 6,171,640; 6,175,060; 6,177,611; 6,225,105; 6,228,623; 6,232,526; 6,252,138; 6,265,638; 6,271,443; 6,294,714; 6,380,462; 6,380,466; 6,384,301; 6,414,222; 6,426,446; 6,426,447; 6,429,357; 6,429,362; 6,433,252; 6,437,217; 6,444,876; 6,459,018; 6,476,295; 6,483,008; 6,489,461; 6,495,739; 6,531,648; 6,537,750; 6,538,178; 6,538,179; 6,538,181; 6,541,259; 6,576,818; 6,589,767; 6,596,538; 6,613,963; 6,635,806; 6,653,530; 6,660,849; 6,706,950; 6,723,837; 6,770,465; 6,774,283; 6,812,379; 6,822,141; 6,828,475; 7,002,058; 7,022,896

U.S. Pat. No. RE37,543

U.S. Patent Application Publication 20050005321; U.S. Patent Application Publication 20060059589; U.S. Patent Application Publication 20030028917; U.S. Patent Application Publication 20030083480; U.S. Patent Application Publication 20030083480; U.S. Patent Application Publication 20030115626; U.S. Patent Application Publication 20030135879; U.S. Patent Application Publication 2003110532; U.S. Patent Application Publication 20040177399; U.S. Patent Application Publication 2005/0005321; U.S. Patent Application Publication 2005/0183170; U.S. Patent Application Publication 20050022261; U.S. Patent Application Publication 2006/0200878; U.S. Patent Application Publication 2007/0271627

Aragon et al., *Plant Sci.* 168:1227-1233, 2005.
Bevan et al., *Nature*, 304:184-187, 1983
Broothaerts et al., *Nature* 433:629-633, 2005.
Callis et al., *Plant Physiol.*, 88:965-968, 1988.
Carrington and Freed, *J. Virology*, 64:1590, 1990.
Chandler et al., *Plant Cell*, 1:1175-1183, 1989
Chu et al., *Sci. Sinica* 18:659-668, 1975.
Chu et al., *Scientia Sinica*, 18:659-668, 1975.
Coruzzi et al., *EMBO J.*, 3:1671-1679, 1984.
Dekeyser et al., *Pl. Physiol.*, 90:217-223, 1989.
Della-Cioppa et al., *Bio/Technology*, 5 579-584, 1987.
Dellaporta et al., In: *Chromosome Structure and Function: Impact of New Concepts*, 18th Stadler Genetics Symposium, 11:263-282, 1988.
Depicker, et al., *J. Mol. Appl. Genet.* 1: 561-574. 1982.
Duncan et al., *Planta* 165:322-332, 1985.s
Elliot et al., *Plant Cell Rep.*, 18:707-714, 1999.
EP 0385 962
EP 275,957
Fraley et al., *Proc. Natl. Acad. Sci. USA*, 80:4803-4807, 1983.
Gamborg et al., *Exp Cell Res.* 50:151-8, 1968.
Ikatu et al., *Bio/Technol.*, 8:241-242, 1990.
Jefferson et al., *Biochem. Soc. Trans.*, 15:7-19, 1987a.
Jefferson et al., *EMBO J.*, 6:3901-3907, 1987b.
Katz et al., *J. Gen. Microbiol.*, 129:2703-2714, 1983.
Klee et al., *Mol. Gen. Genet.*, 210:437-442, 1987.
Kuhlemeier et al., *Plant Cell*, 1:471-478, 1989.
Lawton et al., *Plant Mol. Biol.* 9:315-324, 1987
Linsmaier and Skoog, *Physiol. Plant.* 18: 100-127, 1965.
Linsmaier and Skoog, *Physiol. Plant.*, 18 100, 1965.
Marcotte et al., *Plant Cell*, 1:969-976, 1989
McCabe & Martinell, *Bio/Technology* 11:596-598, 1993.
McCown and Lloyd, *Combined Proc.—Int. Plant Propagator's Soc.*, 30: 421-427, 1981
Miki and McHugh, *J. Biotechnol.*, 107: 193, 2004.
Miki et al., In: *Methods in Plant Molecular Biology and Biotechnology*, Glick and Thompson ((Eds.), CRC Press, Inc., Boca Raton, pages 67-88, 1993.
Murashige and Skoog, *Physiol. Plant.* 15: 473-497, 1962.
Nitsch and Nitsch, *Science* 163:85-87 1969.
Odell et al., *Nature* 313:810-812, 1985
Ow et al., *Science*, 234:856-859, 1986.
PCT Appln. WO 04009761
PCT Appln. WO 04074443
PCT Appln. WO 05003362
PCT Appln. WO 8704181A
PCT Appln. WO8900193A
PCT Appln. WO9215675
PCT Appln. WO9215775
PCT Appln. WO9927116
Schaffner et al., *Plant Cell*, 3:997-1012, 1991
Schenk and Hildebrandt, *Can. J. Bot.* 50:199-204, 1972.
Sutcliffe et al., *Proc. Natl. Acad. Sci. USA*, 75:3737-3741, 1978.
Uchimiya and Murashige, *Plant Physiol.* 15:73, 1962.
Uchimiya and Murashige, *Plant Physiol.* 57: 424-429, 1976.
Walker et al., *Proc. Natl. Acad. Sci. USA*, 84:6624, 1987
Wuni et al., *Plant Cell*, 1:961-968, 1989
Yang et al. *Proc. Natl. Acad. Sci. USA*, 87:4144-4148, 1990
Zambre et al., *Planta* 216:580-586, 2003.
Zukowsky et al., *Proc. Natl. Acad. Sci. USA*, 80:1101-1105, 1983.

What is claimed is:

1. A high-throughput method for producing transformed cotton plant tissue comprising:
   (a) contacting a plurality of cotton embryonic explants with a recombinant *Rhizobium* or *Agrobacterium* spp. capable of transforming at least a first cell of the explant with a selected DNA sequence encoding a selectable marker to obtain at least a first explant transformed with the selected DNA;
   (b) selecting for transgenic tissue by contacting the transformed explant with a selective agent, wherein the selectable marker confers tolerance to the selective agent;
   c) regenerating from at least the first explant transformed with the selected DNA a chimeric cotton plant comprising transgenic plant tissue; and
   d) obtaining a non-chimeric transgenic cotton plant from the transgenic tissue regenerated in step (c);
wherein regenerating the transgenic cotton plant does not comprise generating a callus culture from the explant.

2. The method of claim 1, wherein the explants are stored at a temperature of between 0-15° C. for between 1 hour and 7 days prior to step (a).

3. The method of claim 1, wherein the transgenic cotton plant arises from transformation of a meristem that results in transformation of germline tissue.

4. The method of claim 1, wherein the selected DNA sequence further encodes a screenable marker, or specifies an agronomic trait.

5. The method of claim 1, wherein the explants comprise a transgene prior to step (a).

6. The method of claim 1, wherein the transgenic cotton plant tissue arises from meristem transformation.

7. The method of claim 1, wherein the *Rhizobium* or *Agrobacterium* spp. are suspended in the presence of a selective agent active against an untransformed explant prior to contacting the explants with a recombinant *Rhizobium* or *Agrobacterium* spp.

8. The method of claim 1, wherein, following the contacting of explants with a selected DNA sequence, explants are grown in the presence of a selective agent at 35° C., or are grown under lighting conditions that allow for normal plastid development.

9. The method of claim 8, wherein growth at 35° C. is performed for 1-7 days; the selective agent is selected from the group consisting of spectinomycin, streptomycin, kanamycin, glyphosate, glufosinate, hygromycin, and dicamba; or the explants are grown under a light intensity of >5 μEinsteins with about a 16 hour light/8 dark photoperiod.

10. The method of claim 1, wherein the explants are grown in the presence of a fungicide prior to, during, or subsequent to step (a).

11. The method of claim 10, wherein the explants are grown in the presence of a fungicide and DMSO.

12. The method of claim 11, wherein the explants are grown in the presence of nystatin, thiabendazole, and DMSO.

* * * * *